(12) United States Patent
Derzay et al.

(10) Patent No.: US 6,578,002 B1
(45) Date of Patent: Jun. 10, 2003

(54) MEDICAL DIAGNOSTIC SYSTEM SERVICE PLATFORM

(76) Inventors: Gregory John Derzay, 1136 Turnberry Dr., Pewaukee, WI (US) 53072; John Michael Heinen, 675 N 70th St., Wauwatosa, WI (US) 53213; Cyrillus Tamsil Steven Kunta Hutabarat, 1803 Shepherd Ct. #341, Waukesha, WI (US) 53186; Leo Michael Kucek, 1262 Fox Point Dr., Waukesha, WI (US) 53189; Michael Thomas Suchecki, 903 S. University Dr., Waukesha, WI (US) 53188; David Alan Swierczek, 7073 Blacksmith Ct., Sussex, WI (US) 53089

( * ) Notice: Subject to any disclaimer, the term of this patent is extended or adjusted under 35 U.S.C. 154(b) by 0 days.

(21) Appl. No.: 09/199,665

(22) Filed: Nov. 25, 1998

(51) Int. Cl.[7] .............................................. G06F 17/60
(52) U.S. Cl. ........................... 705/2; 364/563; 128/653; 128/654
(58) Field of Search .................. 705/3, 2; 382/132; 710/8; 378/15, 62; 250/582, 584; 128/784, 653.1, 654, 653.2; 364/563; 356/319; 600/425

(56) References Cited

U.S. PATENT DOCUMENTS

| | | | |
|---|---|---|---|
| 4,847,694 A | | 7/1989 | Nishihara .................... 358/434 |
| 4,958,283 A | | 9/1990 | Tawara et al. .......... 364/413.13 |
| 5,005,126 A | | 4/1991 | Haskin .................. 364/413.13 |
| 5,019,975 A | | 5/1991 | Mukai ................... 364/413.13 |
| 5,140,518 A | | 8/1992 | Ema ....................... 364/413.01 |
| 5,165,411 A | * | 11/1992 | Miyamoto et al. ........ 128/653.2 |
| 5,179,651 A | | 1/1993 | Taaffe et al. ................. 395/154 |
| 5,272,625 A | | 12/1993 | Nishihara et al. ...... 364/413.13 |
| 5,335,172 A | * | 8/1994 | Matsumoto et al. ......... 250/582 |
| 5,335,173 A | * | 8/1994 | Sasahara .................. 128/653.1 |
| 5,359,512 A | | 10/1994 | Nishihara ............... 364/413.01 |
| 5,437,278 A | * | 8/1995 | Wilk ........................ 128/653.1 |
| 5,454,019 A | * | 9/1995 | Migita et al. .................. 378/15 |
| 5,469,353 A | | 11/1995 | Pinsky et al. .......... 364/413.01 |
| 5,479,255 A | * | 12/1995 | Denny et al. ................ 356/319 |
| 5,513,101 A | | 4/1996 | Pinsky et al. ............... 364/401 |
| 5,520,182 A | * | 5/1996 | Leighton et al. ............ 128/654 |
| 5,531,227 A | * | 7/1996 | Schneider ................ 128/653.1 |

(List continued on next page.)

FOREIGN PATENT DOCUMENTS

WO     WO 97/40463    * 10/1997     ........... G06F/17/60

OTHER PUBLICATIONS

Managing Medical Imaging with off–Line Workstations Mueller D–Photonics spectra v23 n12 p95 (3) 12/89.*

Primary Examiner—Vincent Millin
Assistant Examiner—Geoffrey Akers
(74) Attorney, Agent, or Firm—Fletcher, Yoder & Van Someren

(57) ABSTRACT

A uniform service platform is provided for medical diagnostic systems. The platform includes modality interface modules which may be adapted for various system modalities, including magnetic resonance imaging modalities, computed tomography modalities, x-ray modalities, and so forth. A server coordinates the exchange of operational parameter data between the systems and external circuitry, such as a remote service facility. A browser displays user-viewable pages for viewing, requesting and receiving service information. A communications module permits the exchange of service data between a system on which the platform is installed and remote circuitry. The platform may further include a subscription module for verifying subscription and access rights, such as for security purposes. Certain portions of the platform, including the user-viewable pages and modality interface components may be specifically tailored or adapted to the modality of a system on which the platform is installed.

34 Claims, 17 Drawing Sheets

U.S. PATENT DOCUMENTS

| | | | |
|---|---|---|---|
| 5,544,662 A | * 8/1996 | Saulnier et al. | 128/734 |
| 5,572,448 A | * 11/1996 | Judell | 364/563 |
| 5,586,262 A | 12/1996 | Komatsu et al. | 395/200.02 |
| 5,590,164 A | * 12/1996 | Kawai et al. | 378/4 |
| 5,598,185 A | * 1/1997 | Holmgren | 345/153 |
| 5,603,323 A | * 2/1997 | Pflugrath et al. | 128/660.01 |
| 5,604,780 A | * 2/1997 | Nakazawa et al. | 378/62 |
| 5,605,153 A | * 2/1997 | Fujioka et al. | 600/425 |
| 5,616,930 A | * 4/1997 | Janssens et al. | 250/584 |
| 5,617,313 A | * 4/1997 | Namiki | 705/3 |
| 5,644,650 A | * 7/1997 | Suzuki et al. | 382/132 |
| 5,654,555 A | * 8/1997 | Buytaert et al. | 250/581 |
| 5,655,084 A | 8/1997 | Pinsky et al. | 395/203 |
| 5,655,532 A | * 8/1997 | Yasugi et al. | 128/653.2 |
| 5,673,332 A | * 9/1997 | Nishikawa et al. | 382/128 |
| 5,675,744 A | 10/1997 | Tsujii | 395/203 |
| 5,682,549 A | * 10/1997 | Tanaka et al. | 710/8 |
| 5,715,823 A | 2/1998 | Wood et al. | 128/660.01 |
| 5,779,634 A | 7/1998 | Ema et al. | 600/407 |
| 5,790,793 A | 8/1998 | Higley | 395/200.48 |

* cited by examiner

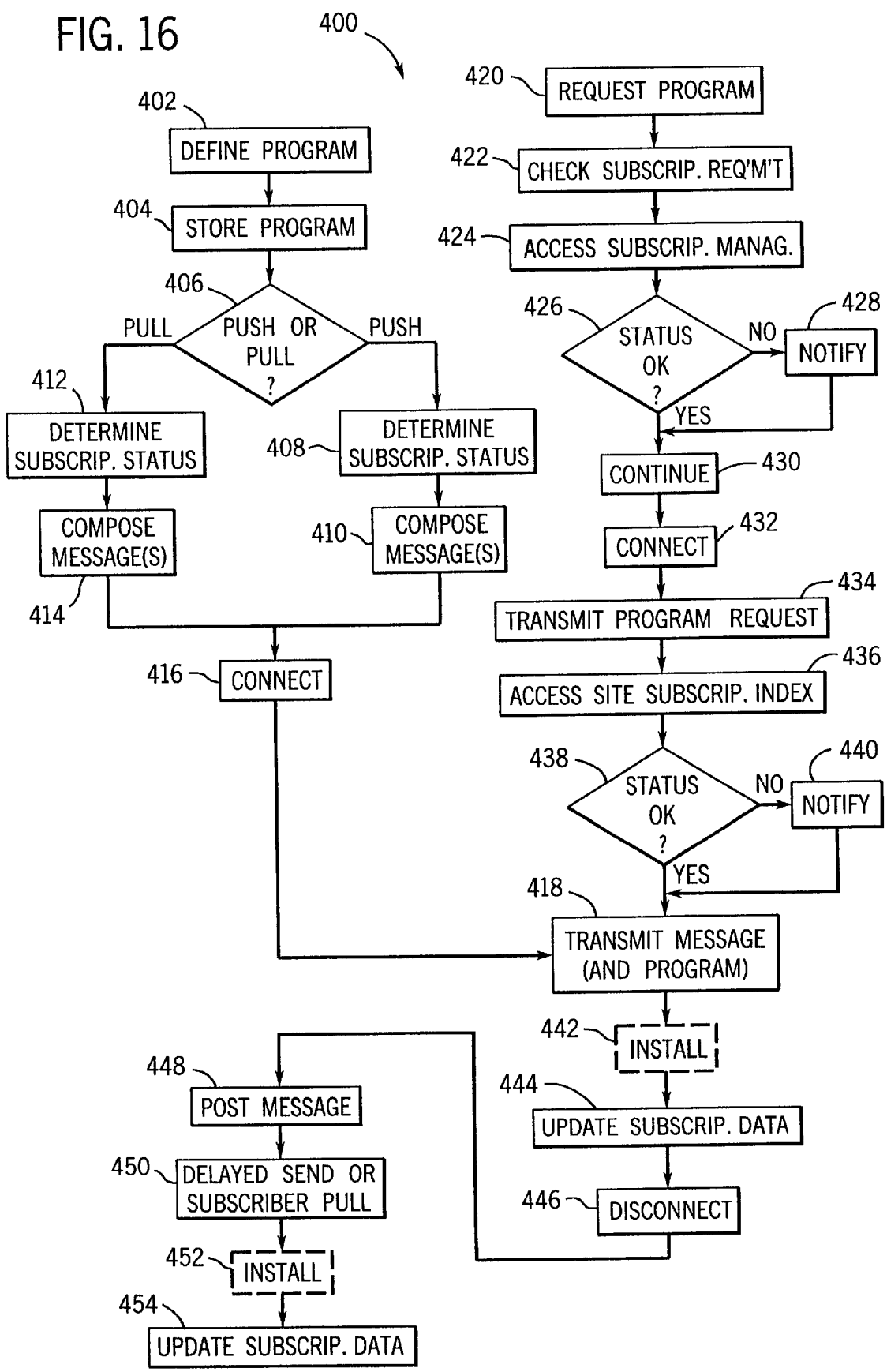

MEDICAL DIAGNOSTIC SYSTEM SERVICE PLATFORM

FIELD OF THE INVENTION

The present invention relates generally to the field of medical diagnostic systems, such as imaging systems. More particularly, the invention relates to a service platform for facilitating remote servicing of medical diagnostic systems, such as through interactive communication with a centralized service facility. The platform may be implemented through software, hardware, firmware, or a combination of these.

BACKGROUND OF THE INVENTION

Medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both conventional and digital or digitized imaging systems), magnetic resonance (MR) systems, positron emission tomography (PET) systems, ultrasound systems, nuclear medicine systems, and so forth. In many instances, these modalities complement one another and offer the physician a range of techniques for imaging particular types of tissue, organs, physiological systems, and so forth. Health care institutions often dispose of several such imaging systems at a single or multiple facilities, permitting its physicians to draw upon such resources as required by particular patient needs.

Modern medical diagnostic systems typically include circuitry for acquiring image data and for transforming the data into a useable form which is then processed to create a reconstructed image of features of interest within the patient. The image data acquisition and processing circuitry is often referred to as a "scanner" regardless of the modality, because some sort of physical or electronic scanning often occurs in the imaging process. The particular components of the system and related circuitry, of course, differ greatly between modalities due to their different physics and data processing requirements.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by remote service centers capable of contacting scanners at subscribing institutions directly without the need for intervention on the part of the institution personnel. Such remote servicing is intended to maintain the diagnostic systems in good operational order without necessitating the attention of physicians or radiologists, and is often quite transparent to the institution.

In certain remote servicing systems, a computerized service center may contact a scanner via a network to check system configurations and operational states, to collect data for report generation, and to perform other useful service functions. Such contacts can be made periodically, such as during system "sweeps" in which a variety of system performance data is collected and stored with historical data for the particular scanner. The data can then be used to evaluate system performance, propose or schedule visits by service personnel, and the like.

While such service techniques have proven extremely valuable in maintaining diagnostic systems, further improvements are still needed. For example, in conventional service systems, contact between the scanners and a centralized service center most often originates with the service center. The scanners are provided with only limited functionality in the ability to identify and define service needs. Even where the scanners have permitted some limited ability to contact networked service providers, intermittent conditions indicative of a potentially serviceable problem may cease by the time the service provider is contacted or recontacts the scanner after a service call. Moreover, although the transparency of interactions between scanners and service centers avoids unnecessarily distracting medical personnel with service updates, it has become apparent that some degree of interaction between service centers and institutions would be highly desirable. In particular, an interactive service system would facilitate valuable exchanges of information, including reports of system performance, feedback on particular incidents requiring attention, updates of system licenses, software, imaging protocols, and so forth. Currently available service systems do not permit such interactive exchanges.

In addition to the foregoing drawbacks, conventional scanners are not suitably adapted to support user-friendly, scanner-based service exchanges. User interfaces in such scanners typically only permit limited access to service information, and do not provide a particularly useful interface for identifying and defining serviceable conditions as they occur. Moreover, software platforms and interfaces in conventional scanners are not suitable for interaction with service centers, and generally exclude the user from communications between the scanner and the service center or, conversely, impose unnecessarily on the user by requiring intervention for certain service functions such as software updates or downloads. Furthermore, platforms have yet to be developed that can serve as a base for interactive servicing needs of different modalities. Rather, such platforms have traditionally been specifically designed for the needs of a particular modality or even a particular scanner with little cross utility between systems or modalities.

While certain improvements in diagnostic stations has been made for certain modalities, these are still insufficient to satisfy the current need. For example, graphical user interfaces are available for specific modality scanners, such as ultrasound scanners, which enable software downloads and remote access to images. The remote access features are, however, generally limited to transmitting image configurations and image data for reconstruction between remote physician workstations and the scanner. At present, no systems provide for exchanging information on possible service problems with the scanners, or information or data log files for the purpose of providing remote service of the scanner itself.

SUMMARY OF THE INVENTION

The present invention provides a service platform for medical diagnostic systems designed to respond to these needs. The platform may be implemented through specific hardware, firmware, software, or a combination, depending upon the preferred configuration of the scanners. The platform preferably provides a uniform and consistent basis for configuring interactive service routines over a wide range of scanner types, and system modalities. The platform may be implemented directly in computers coupled to the scanners, and may also be installed in centralized control stations, such as stations linking a series of scanners in a radiology department of a medical facility.

The platform may consist of a number of functional units. For example, in a preferred configuration, the platform includes a browser useful for operations personnel to navigate through service information and requests, as well as to interactively exchange service information with a centralized service center. A server in the platform then facilitates exchange of service information and system data with the centralized service center. The platform may also include internal security components which verify the right to exchange of certain information between the scanner and the service center. Such security components may verify user licenses, software configurations, and so forth. The platform also preferably includes a series of tools which facilitate configuration of the platform for use with a wide variety of diagnostic system types and modalities. The platform may thereby be adapted for use in various systems, while providing uniformity in file designations, signal flow, connectivity protocols, and so forth.

DETAILED DESCRIPTION OF THE INVENTION

Figure 1:
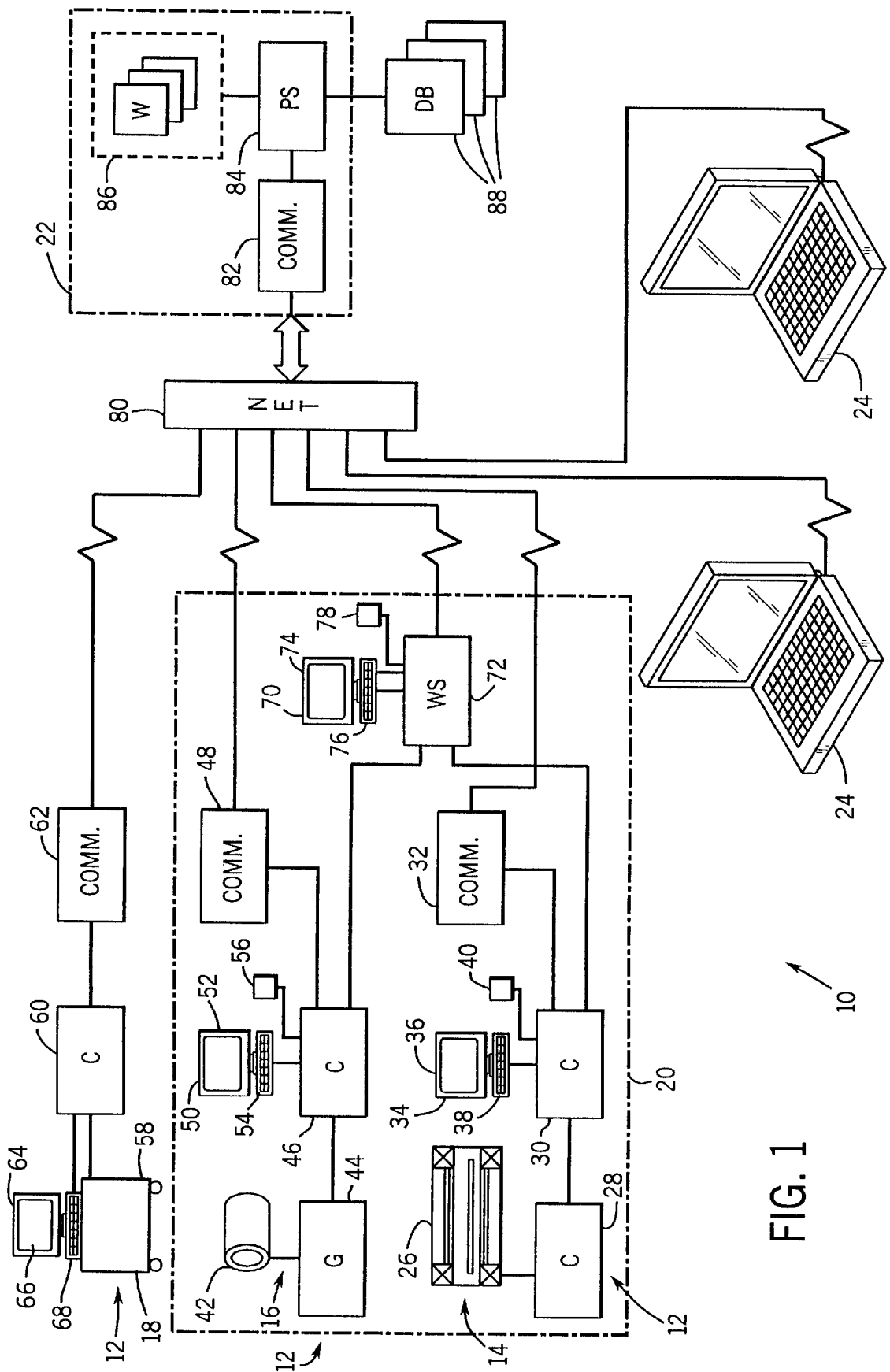
FIG. 1 is a diagrammatical representation of a series of medical diagnostic systems coupled to a service facility via a network connection for providing remote service and data interchange between the diagnostic systems and the service facility.

Turning now to the drawings, and referring first to FIG. 1, a service system 10 is illustrated for providing remote service to a plurality of medical diagnostic systems 12. In the embodiment illustrated in FIG. 1, the medical diagnostic systems include a magnetic resonance imaging (MRI) system 14, a computed tomography (CT) system 16, and an ultrasound imaging system 18. The diagnostic systems may be positioned in a single location or facility, such as a medical facility 20, or may be remote from one another as shown in the case of ultrasound system 18. The diagnostic systems are serviced from a centralized service facility 22. Moreover, a plurality of field service units 24 may be coupled in the service system for transmitting service requests, verifying service status, transmitting service data and so forth as described more fully below.

In the exemplary embodiment of FIG. 1, several different system modalities are provided with remote service by the service facility. These and other modalities may be similarly serviced by the service facility, depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRJ systems, CT systems, ultrasound systems, positron emission tomography (PET) systems, nuclear medicine systems, and so forth. Moreover, the various modality systems serviced in accordance with the present techniques may be of different type, manufacture, and model. Service requests and data transmitted between the systems and the service facility includes data for identifying the type and modality of the serviced system, as well as data specifically adapted to the system modality and model. It should also be noted that, as used herein, the term "service request" is intended to include a wide range of inquiries, comments, suggestions and other queries or messages generated by a diagnostic system or an institution in which a system is disposed or managed. In particular, such requests may relate to problems occurring on systems, applications questions, questions of a general nature, questions relating to financial or subscription arrangements, information sharing, reports, applications, protocols, and so forth.

Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. System controller 30 includes a uniform platform for interactively exchanging service requests, messages and data with service facility 22 as described more fully below. System controller 30 is linked to a communications module 32, which may be included in a single or separate physical package from system controller 30. System controller 30 is also linked to an operator station 34 which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment benefiting from the present techniques may include imaging systems, clinical diagnostic systems, physiological monitoring systems and so forth.

Similarly, CT system 16 will typically include a scanner 42 which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for remote service of system 16. Also, system controller 46 is coupled to an operator station 50 which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting service requests, messages and data between system controller 60 and service facility 22. System 18 also includes an operators station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated embodiment. The management system may include a computer workstation or personal computer 72 coupled to the system controllers in an intranet configuration, in a file sharing configuration, a client/server arrangement, or in any other suitable manner. Moreover, management station 70 will typically include a monitor 74 for viewing system operational parameters, analyzing system utilization, and exchanging service requests and data between the facility 20 and the service facility 22. Input devices, such as a standard computer keyboard 76 and mouse 78, may also be provided to facilitate the user interface. It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 72 and field service units 24 may be linked to service facility 22 via a remote access network 80. For this purpose, any suitable network connection may be employed. Presently preferred network configurations include both proprietary or dedicated networks, as well as open networks, such as the Internet. Data may be exchanged between the diagnostic systems, field service units, and remote service facility 22 in any suitable format, such as in accordance with the Internet Protocol (EP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 22, messages, service requests and data are received by communication components as indicated generally at reference numeral 82. Components 82 transmit the service data to a service center processing system, represented generally at reference numeral 84 in FIG. 1. The processing system manages the receipt, handling and transmission of service data to and from the service facility. In general, processing system 84 may include one or a plurality of computers, as well as dedicated hardware or software servers for processing the various service requests and for receiving and transmitting the service data as described more fully below. Service facility 22 also includes a bank of operator workstations 86 which may be staffed by service engineers who address the service requests and provide off and on-line service to the diagnostic systems in response to the service requests. Also, processing system 84 may be linked to a system of databases or other processing systems 88 at or remote from the service facility 22. Such databases and processing systems may include extensive database information on operating parameters, service histories, and so forth, both for particular subscribing scanners, as well as for extended populations of diagnostic equipment. As described below, such databases may be employed both for servicing of particular diagnostic systems and for tracking such servicing, as well as for deriving comparison data for use in servicing a particular system or a family of systems.

Figure 2:
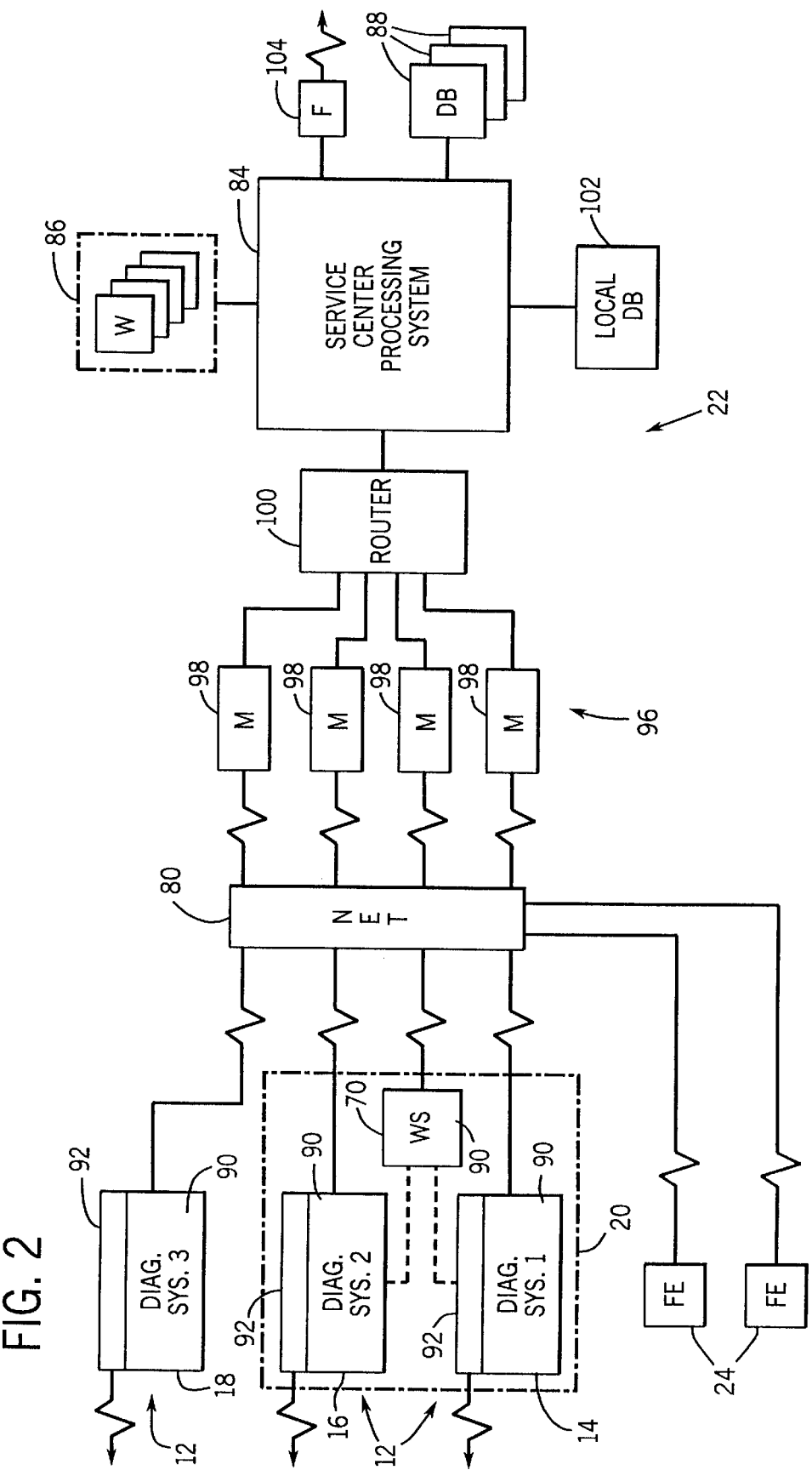
FIG. 2 is a block diagram of the systems shown in FIG. 1 illustrating certain functional components of the diagnostic systems and the service facility.

FIG. 2 is a block diagram illustrating the foregoing system components in a functional view. As shown in FIG. 2, the field service units 24 and the diagnostic systems 12 can be linked to the service facility 22 via a network connection as illustrated generally at reference numeral 80. Within each diagnostic system 12, a uniform service platform 90 is provided. Platform 90, which is described in greater detail below with particular reference to FIG. 3, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 70 is provided, a similar uniform platform is preferably loaded on the management station to facilitate direct interfacing between the management station and the service facility. In addition to the uniform service platform 90, each diagnostic system is preferably provided with an alternative communications module 92, such as a facsimile transmission module for sending and receiving facsimile messages between the scanner and remote service facilities.

Messages and data transmitted between the diagnostic systems and the service facility traverse a security barrier or "firewall" contained within processing system 84 as discussed below, which prevents unauthorized access to the service facility in a manner generally known in the art. A modem rack 96, including a series of modems 98, receives the incoming data, and transmits outgoing data through a router 100 which manages data traffic between the modems and the service center processing system 84.

As mentioned above, processing system 84 receives and processes the service requests and data, and interfaces with additional service components, both at the service facility and remote from the facility. In the diagram of FIG. 2, operator workstations 86 are coupled to the processing system, as are remote databases or computers 88. In addition, at least one local service database 102 is provided for verifying license and contract arrangements, storing service record files, log files, and so forth. Moreover, one or more communication modules 104 are linked to processing system 84 to send and receive facsimile transmissions between the service facility and the diagnostic systems or field service units.

Figure 3:
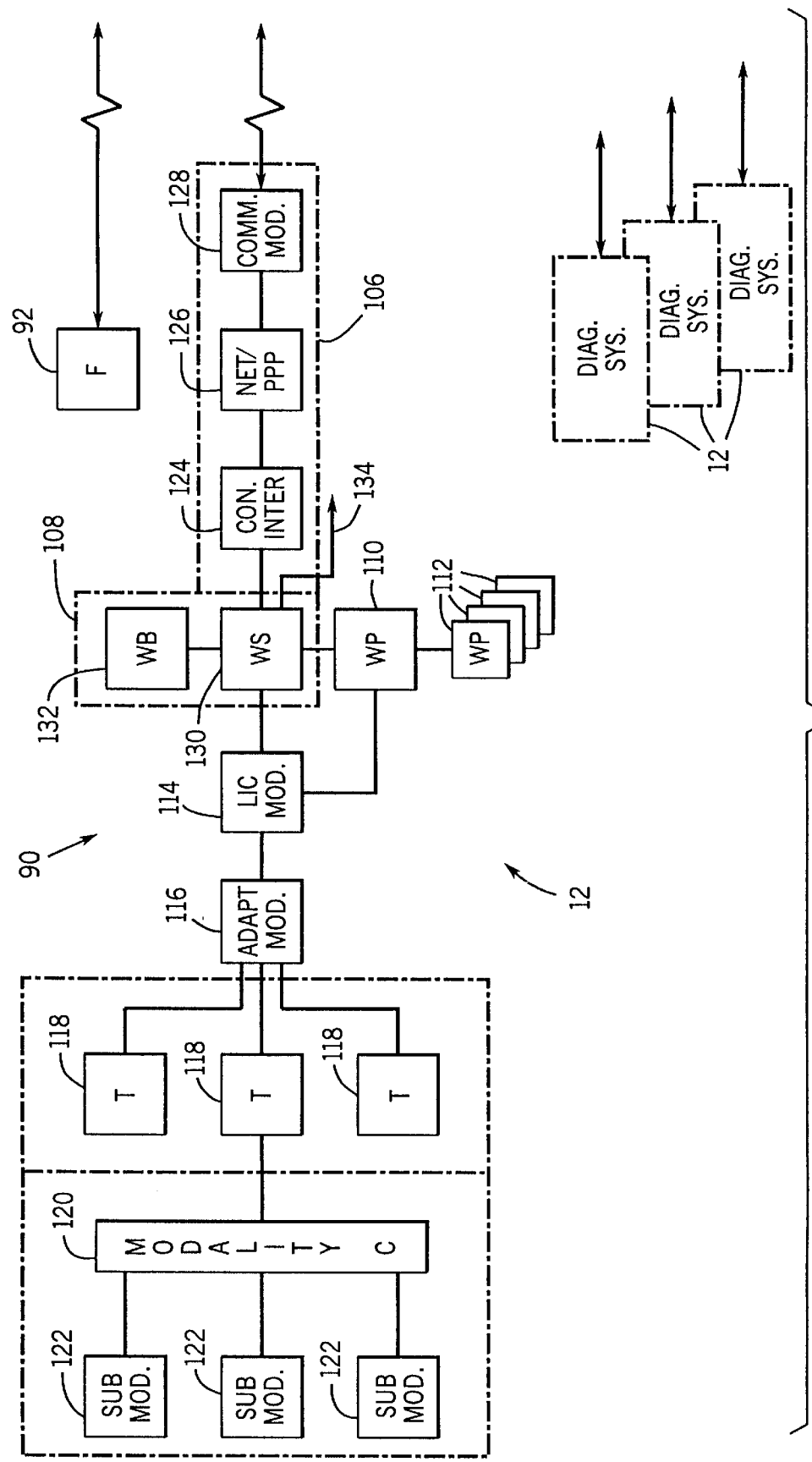
FIG. 3 is a block diagram of certain functional components within a diagnostic system of the type shown in FIG. 1 and FIG. 2 for facilitating interactive remote servicing of the diagnostic system.

FIG. 3 illustrates diagrammatically the various functional components comprising the uniform service platform 90 within each diagnostic system 12. As shown in FIG. 3, the uniform platform includes a device connectivity module 106, as well as a network connectivity module 108. Network connectivity module 108 accesses a main web page 110 which, as mentioned above, is preferably a markup language page, such as an HTML page displayed for the system user on a monitor at the diagnostic system. Main web page 110 is preferably accessible from a normal operating page in which the user will configure examination requests, view the results of examinations, and so forth such as via an on-screen icon. Through main web page 110, a series of additional web pages 112 are accessible. Such web pages permit service requests to be composed and transmitted to the remote service facility, and facilitate the exchange of other messages, reports, software, protocols, and so forth as described more fully below. It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 108 is coupled to a license module 114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 114 is, in turn, coupled to one or more adapter utilities 116 for interfacing the browser, server, and communications components with modality interface tools 118. In a presently preferred configuration, several such interface tools are provided for exchanging data between the system scanner and the service platform. For example, modality interface tools 118 may include applets or servlets for building modality-specific applications, as well as configuration templates, graphical user interface customization code, and so forth. Adapters 116 may interact with such components, or directly with a modality controller 120 which is coupled to modality-specific subcomponents 122. The modality controller 120 and modality-specific subcomponents 122 will typically include a preconfigured processor or computer for executing examinations, and memory circuitry for storing image data files, log files, error files, and so forth. Adapter 116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 106 includes several components for providing data exchange between the diagnostic system and the remote service facility. In particular, a connectivity service module 124 provides for interfacing with network connectivity module 108. A Point-to-Point Protocol (PPP) module 126 is also provided for transmitting Internet Protocol (IP) packets over remote communication connections. Finally, a modem 128 is provided for receiving and transmitting data between the diagnostic system and the remote service facility. As will be appreciated by those skilled in the art, various other network protocols and components may be employed within device connectivity module 106 for facilitating such data exchange.

Network connectivity module 108 preferably includes a server 130 and a browser 132. Server 130 facilitates data exchange between the diagnostic system and the service facility, and permits a series of web pages 110 and 112 to be viewed via browser 132. In a presently preferred embodiment, server 130 and browser 132 support HTTP applications and the browser supports java applications. Other servers and browsers, or similar software packages may, of course, be employed for exchanging data, service requests, messages, and software between the diagnostic system, the operator and the remote service facility. Finally, a direct network connection 134 may be provided between server 130 and an operator workstation, such as management station 70 within the medical facility (see FIGS. 1 and 2).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility. Features of the application are segmented into separate tabbed pages accessible by the service engineer. The application is entered via a license agreement screen. Once accepted, the service engineer can configure parameters of the system modem, the schedule for running automatic diagnostic checks, and establish electronic messaging, such as for automatic service report generation. Once the modem is configured, the service engineer establishes contact with the service facility and provides data enabling the service facility to download any remaining data needed for secure communication between the system and the service center. Upon exit from the application, a configuration status is presented to the service engineer, including status of an automatic test of connectivity between the sites.

Figure 4:
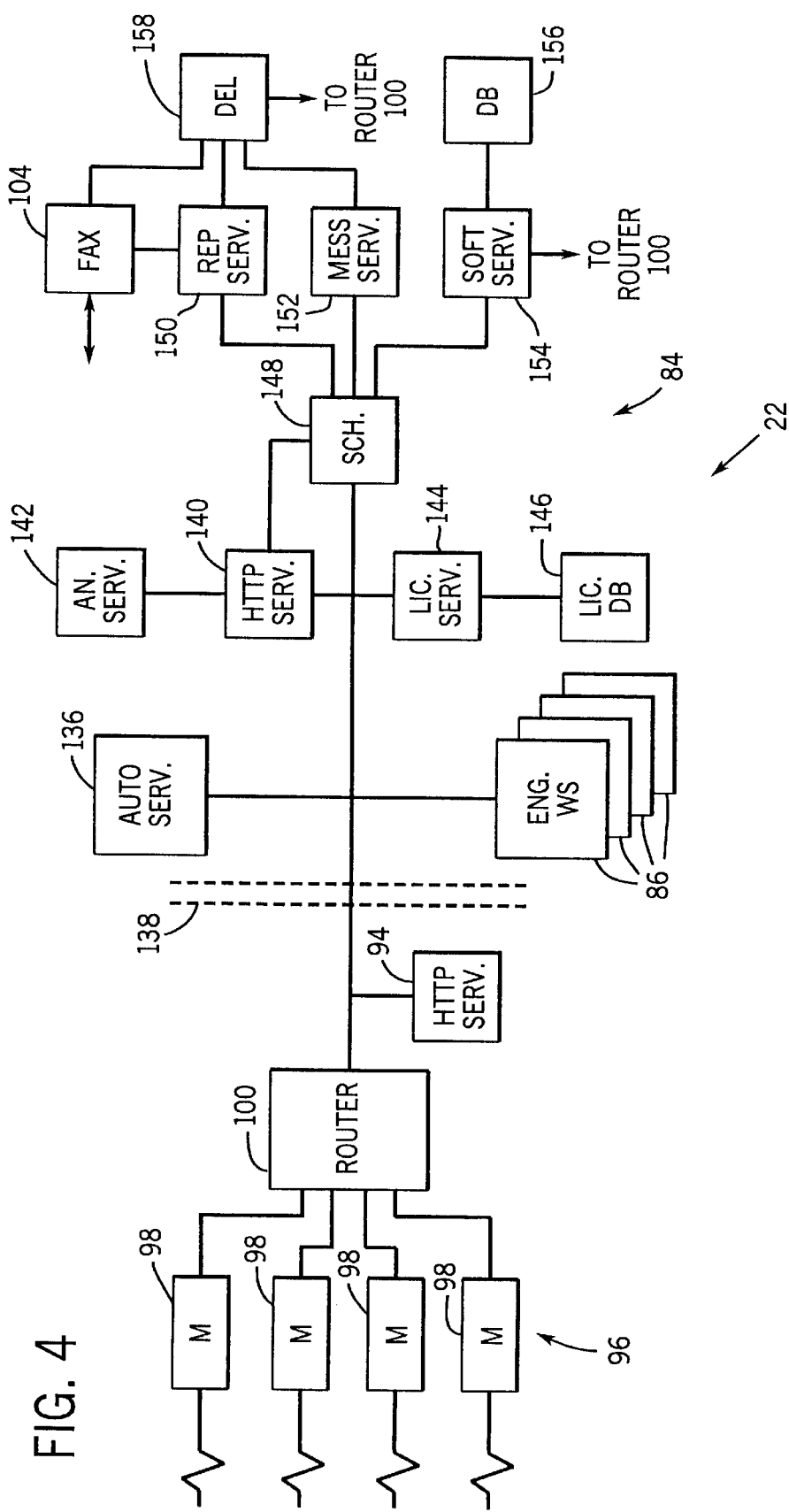
FIG. 4 is a block diagram of certain of the functional components of the service facility illustrated in FIG. 1 and FIG. 2 for rendering interactive remote service to a plurality of medical diagnostic systems.

FIG. 4 illustrates exemplary functional components for service facility 22. As indicated above, service facility 22 includes a modem rack 96 comprising a plurality of modems 98 coupled to a router 100 for coordinating data communications with the service facility. An HTTP service server 94 receives and directs incoming and outgoing transactions with the facility. Server 94 is coupled to the other components of the facility through a firewall 138 for system security. Operator workstations 86 are coupled to the port manager for handling service requests and transmitting messages and reports in response to such requests. An automated service unit 136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 84. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 138, an HTTP application server 140 coordinates handling of service requests, messaging, reporting, software transfers and so forth. Other servers may be coupled to HTTP server 140, such as service analysis servers 142 configured to address specific types of service requests, as described more fully below. In the illustrated embodiment, processing system 84 also includes a license server 144 which is coupled to a license database 146 for storing, updating and verifying the status of diagnostic system service subscriptions. Alternatively, where desired, license server 144 may be placed outside of fire wall 138 to verify subscription status prior to admission to the service facility.

Handling of service requests, messaging, and reporting is further coordinated by a scheduler module 148 coupled to HTTP server 140. Scheduler module 148 coordinates activities of other servers comprising the processing system, such as a report server 150, a message server 152, and a software download server 154. As will be appreciated by those skilled in the art, servers 150, 152 and 154 are coupled to memory devices (not shown) for storing data such as addresses, log files, message and report files, applications software, and so forth. In particular, as illustrated in FIG. 4, software server 154 is coupled via one or more data channels to a storage device 156 for containing transmittable software packages which may be sent directly to the diagnostic systems, accessed by the diagnostic systems, or supplied on pay-per-use or purchase basis. Message and report servers 152 and 154 are further coupled, along with communications module 104, to a delivery handling module 158, which is configured to receive outgoing messages, insure proper connectivity with diagnostic systems, and coordinate transmission of the messages.

Figure 4A:
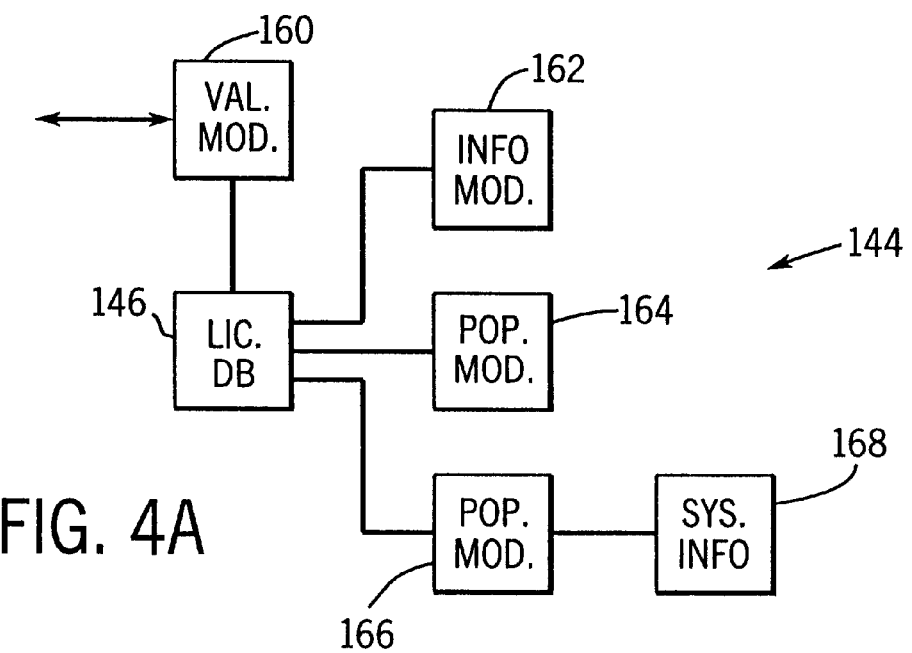
FIGS. 4(A) and 4(B) illustrate sub-components for license and report servers included in the processing system shown in FIG. 4.
Figure 4B:
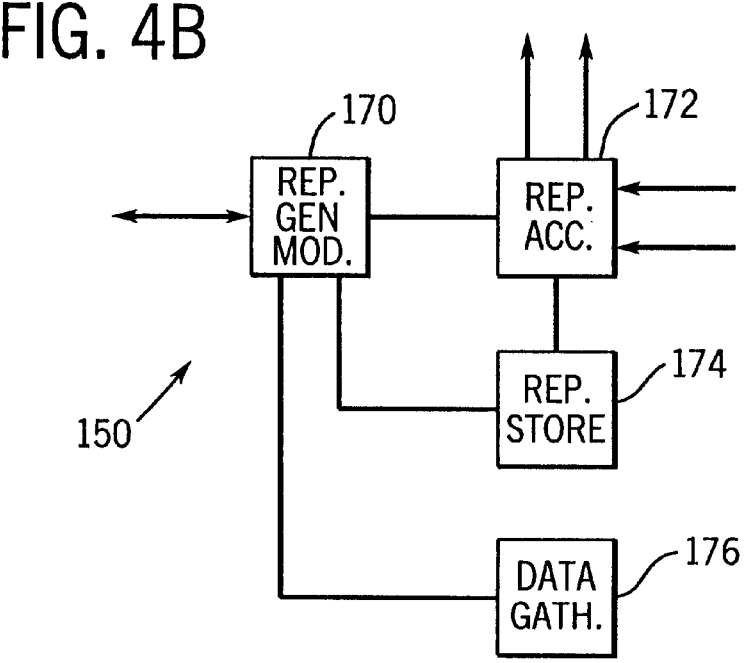

The foregoing components may, of course, include further subcomponents for executing specific functions in the processing system. FIGS. 4A and 4B illustrate such subcomponents for license server 144 and report server 150. As shown in FIG. 4A, license server 144 includes a validity check module 160 linked to license database 146. The license database is further linked to a key information module 162, a contract population process module 164, and a site population process module 166. The latter module is further coupled to systemic information databases 168. As described more fully below, validity check module 160 receives site information, verifies site and license information with license database 146, and accesses resulting status information from the database. Module 160 then may output the site status and license status information to the HTTP server within the processing system for enabling consideration and response to a service request or for otherwise addressing the service request. Module 162 receives key information and site information regarding the particular diagnostic system requesting service, and transmits site identification, configuration, and similar information to other system components through the intermediary of database 146. Similarly, population process modules 164 and 166 store and provide general contract status data, service security keys, site demographic information, and so forth.

The functional components of report server 150, as shown in FIG. 4B, may include a report generation module 170, coupled to a report access module 172, a report storage device 174, and an automated data gathering module 176. Automated data gathering module 176 may include all or a portion of an automated service unit 136 as shown in FIG. 4. As described more fully below, the components of the report server receive scanner data, service information, warehouse information, and the like, and generate system-specific reports based upon this and collected information, such as from gathering module 176. Such reports may also include information on entire populations of similar diagnostic systems, such as for comparison purposes, component life predictions and so forth. The reports may be stored and accessed remotely by the diagnostic system as described below.

Figure 5:
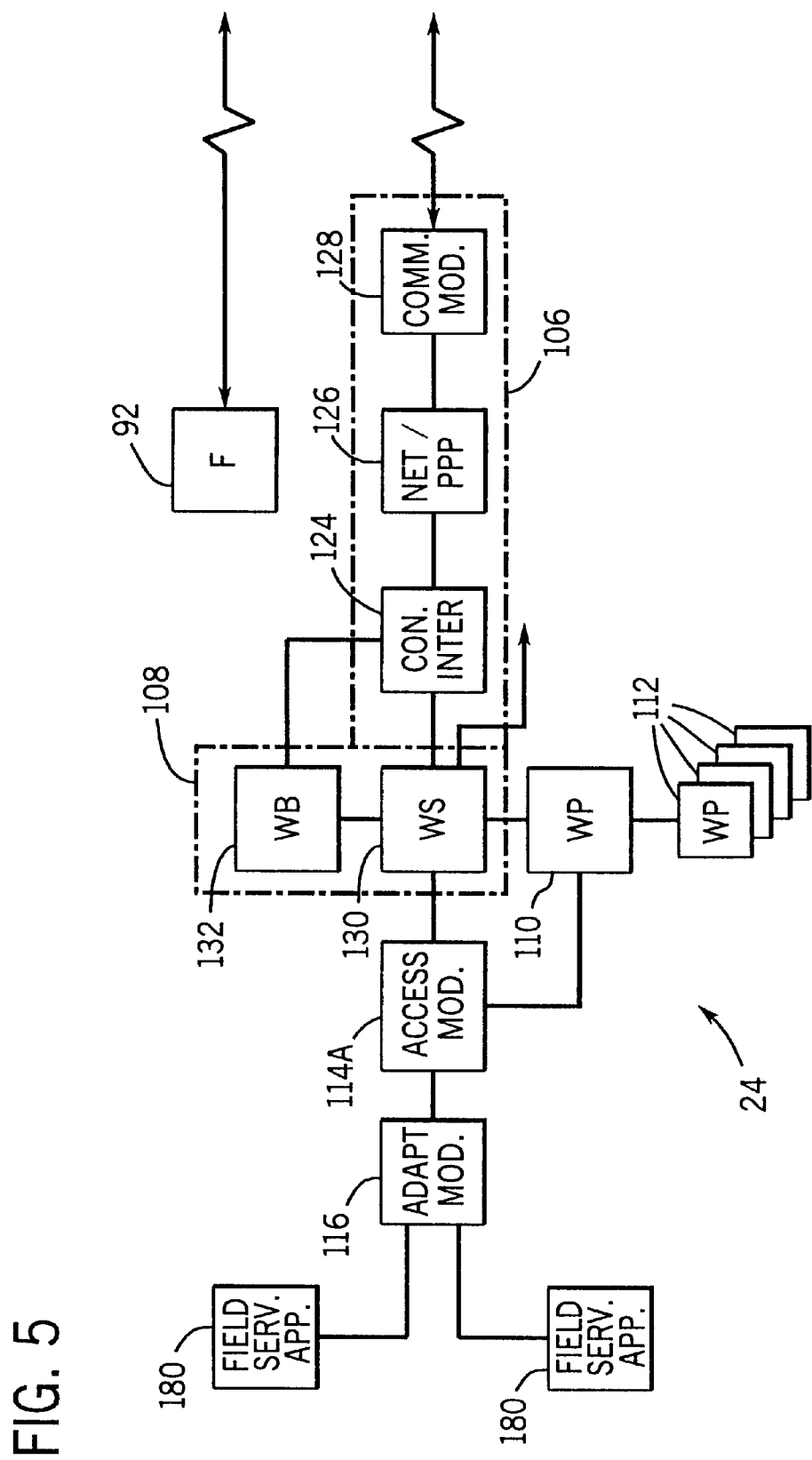
FIG. 5 is a block diagram of functional components within a field service unit which can be coupled to the diagnostic systems and to the service facility for exchanging service information with a field service engineer.
Figure 6:
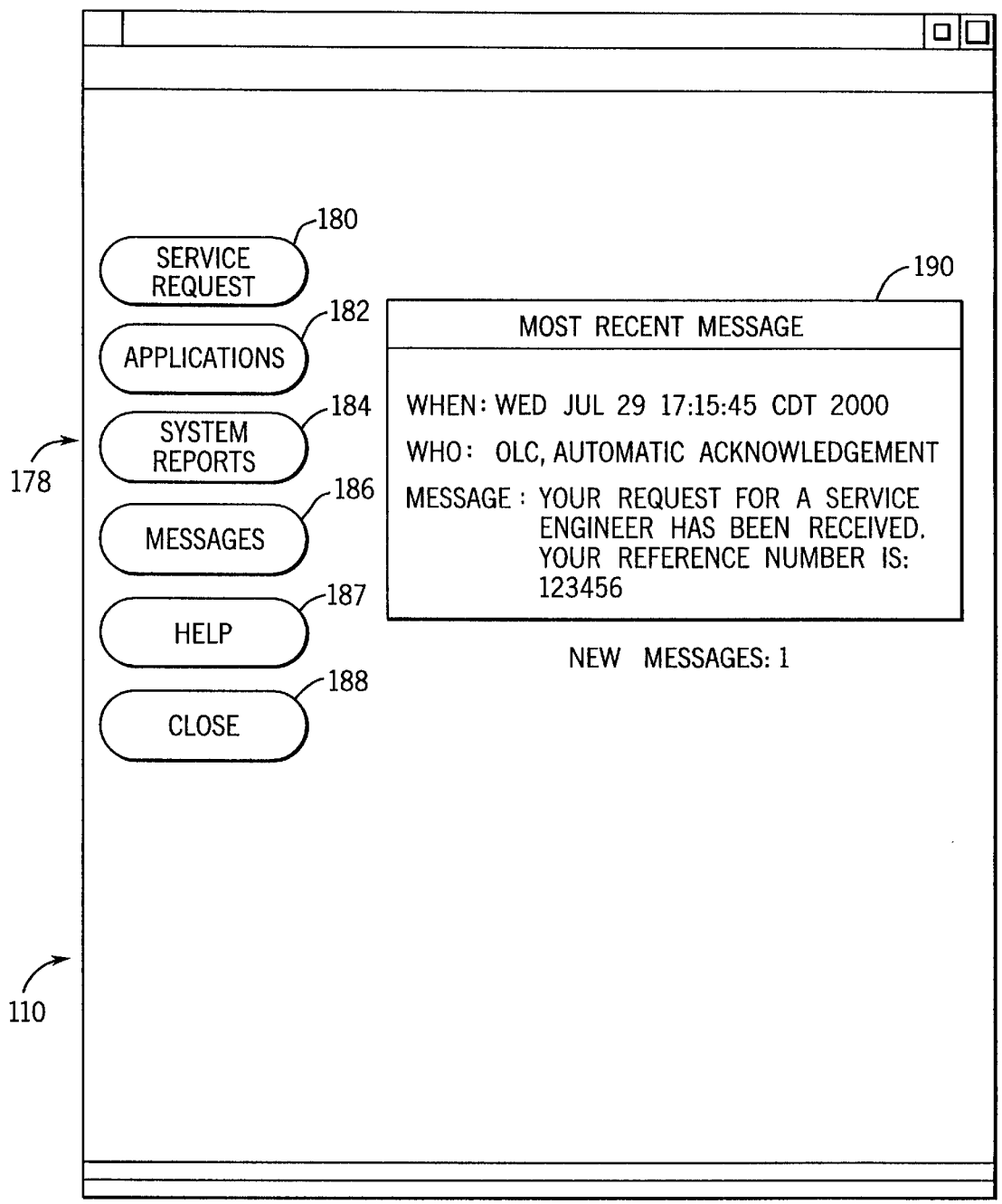
FIG. 6 is an exemplary user interface page incorporated in the diagnostic system for placing service requests, and sending and receiving service data between the diagnostic system and a remote service facility.

FIG. 5 illustrates certain of the functional components contained within an exemplary field service unit 24. Field service unit 24 may include a portable computer designed for use by remote service engineers. The unit includes a service platform which includes certain functional circuitry for establishing a uniform service base as discussed above for the diagnostic systems themselves. Moreover, the service units include specific service tools which enable the field engineer to request and receive remote service messages, reports on specific diagnostic systems, service schedules, and so forth. Through the service platform, therefore, the field engineer may access system configurations, historic log information, system network information, analysis logs and data, and so forth. In addition, the field service unit described below, in conjunction with the system platform and the service facility components, permits such information to be accessed either by the field engineer on the field service unit, or at the diagnostic system itself (e.g. when the service engineer is on-site), or from the remote service facility. The field engineer may also update service records either from the field service unit or from the diagnostic system, as desired.

Thus, as shown in FIG. 5, an exemplary field service unit includes a device connectivity module 106 and a network connectivity module 108. Device connectivity module 106 may include connectivity interface circuitry 124, a network or PPP module 126, and a modem 128, as described above for the diagnostic system with reference to FIG. 3. The network connectivity module 108 may, in turn, include a server 130 and browser 132 substantially identical to those of the diagnostic systems, enabling the field engineer to receive, view and compose messages, reports, and so forth via a main web page 110 and a series of web pages 112. Moreover, an access module 114A is provided for allowing the service facility to verify the license and security status of the field service unit. For example, the access module, in cooperation with circuitry at the service facility, may permit a field service engineer to access data or applications providing some or all of the functionality offered to service engineers at the service facility. Such functionalities may be similar to those provided at the diagnostic systems themselves, or may offer the service engineer a wider range of service options. One or more adapter modules 116 provide for interfacing the network circuitry with various field service tools. In particular, the field service unit may be equipped with service applications, as indicated at blocks 180, such as for analyzing diagnostic system performance data, scheduling regular or special service calls, scheduling for shipment of replacement parts, and so forth. Other service applications may include applications generally similar to those executed on the operator workstations 86 of the service facility (see, e.g. FIG. 4). Such applications may permit the field service engineer to address service requests at the diagnostic system site, or remote from the site as required, and transmit service messages and updates via the remote field service unit.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. FIGS. 6 through 11 illustrate exemplary pages for providing interactive information, composing service requests, selecting and transferring messages, reports and diagnostic system software, and so forth. It should be noted that through the following discussion, reference is made to viewable pages for interfacing in the language of the present description. However, in a presently preferred embodiment, the platform may be configured to present such interface pages in several different languages, depending upon the country in which the system is installed. As illustrated first in FIG. 6, a main web page 110 is accessible from a normal diagnostic system screen viewable on the diagnostic system monitor 36, 52 or 66. Main web page 110 may therefore be viewable by clicking an input device such as a mouse on an icon (not shown) on the normal operational screen. Main web page 110 includes a series of navigation devices 178 in the form of graphical buttons for accessing other interface pages in the graphical user interface. In the illustrated embodiment, these graphical devices include a service request button 180 for accessing a service request page, an applications button 182 for accessing an applications page, a system reports button 184 for accessing service reports, and a messages button 186 for sending and receiving interactive service messages. A help button 187 is provided for accessing user information, help topics and so forth, which may be resident on the system, or available through on-line sources viewable through the system browser. A close or exit button 188 is provided for returning to the normal scanner interface page. In addition to these navigational devices, main page 110 includes a message area 190 in which information regarding the most recent messages is displayed. This information may include identification of the time and date received, the originator of the message, and a brief summary of the message content or title. Thus, upon accessing main page 110, the system user is made aware of service activities carried out by the remote service facility or field service engineer.

Figure 7:
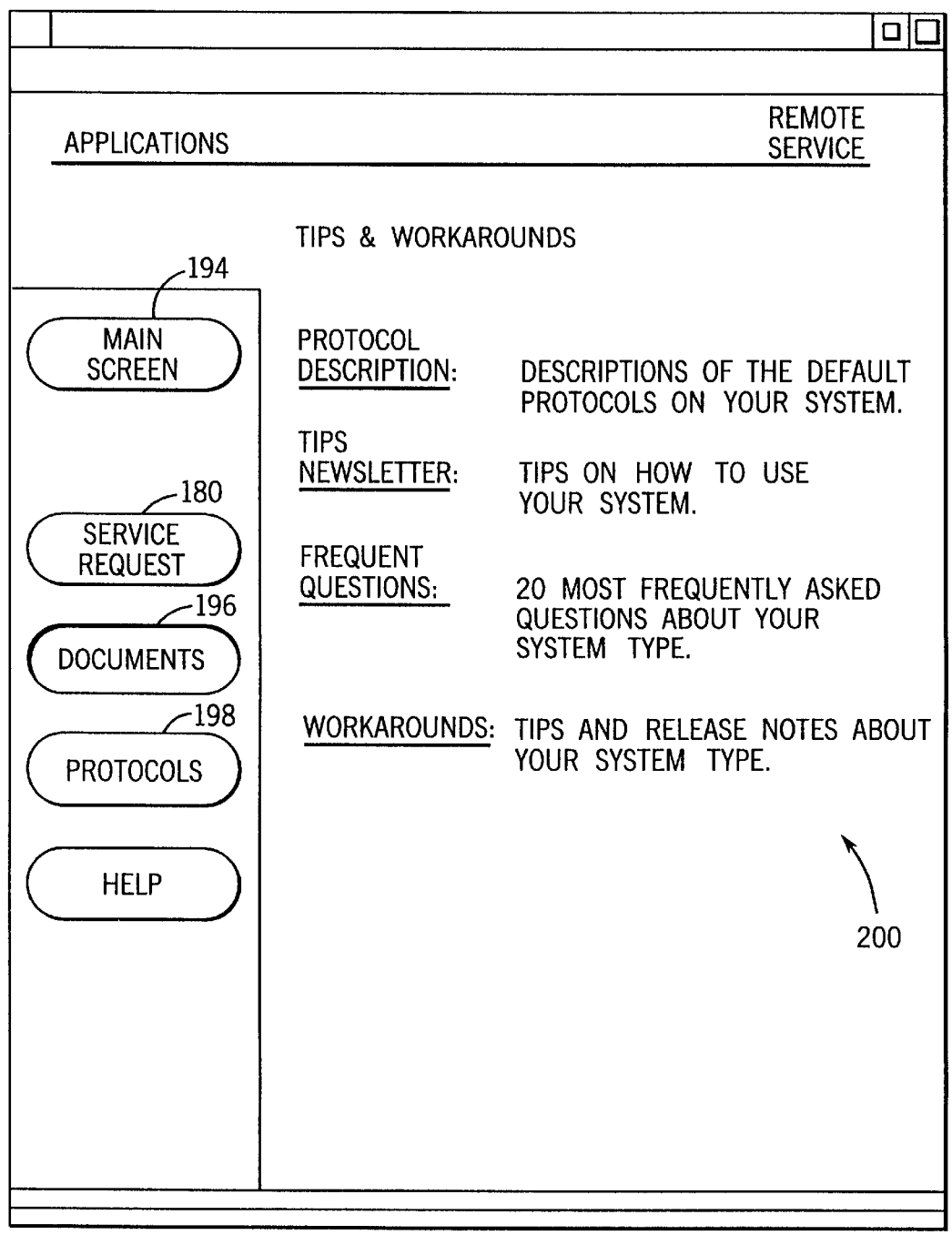
FIG. 7 is a second user interface page for conveying service information to the scanner operator from the service facility.

FIG. 7 illustrates the applications page 192 accessed by actuation of the applications button 182 in the main page. As in the main page, the applications page includes a series of graphical buttons 178 for navigating through the other pages of the graphical user interface, including a main screen button 194 for returning to the main screen shown in FIG. 6. Moreover, additional web pages may be accessible through the applications page, such as a documentation or a help page or series of pages, accessible through a graphical button 196. A protocols page is accessible through a graphical button 198. Moreover, page 192 is provided with a text area 200 in which text describing various service documentation, messages, modality equipment, operational instructions, and so forth may be displayed.

It should be noted that in a presently preferred configuration, the information displayed within text area 200 is specifically designed for the particular modality and type of diagnostic system on which the uniform platform is installed. Thus, as described below, when the service center is placed into network contact with the diagnostic system, the identification of the diagnostic system to the service center allows the service center to transmit and display modality-specific information in the text area. In the embodiment illustrated in FIG. 7, such text includes documentation on imaging protocol or examination descriptions, a system newsletter specifically adapted for the modality and system type, updated questions and answers, and instructional suggestions for operation of the diagnostic system. The user can access the specific documents described in the text area by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Figure 8:
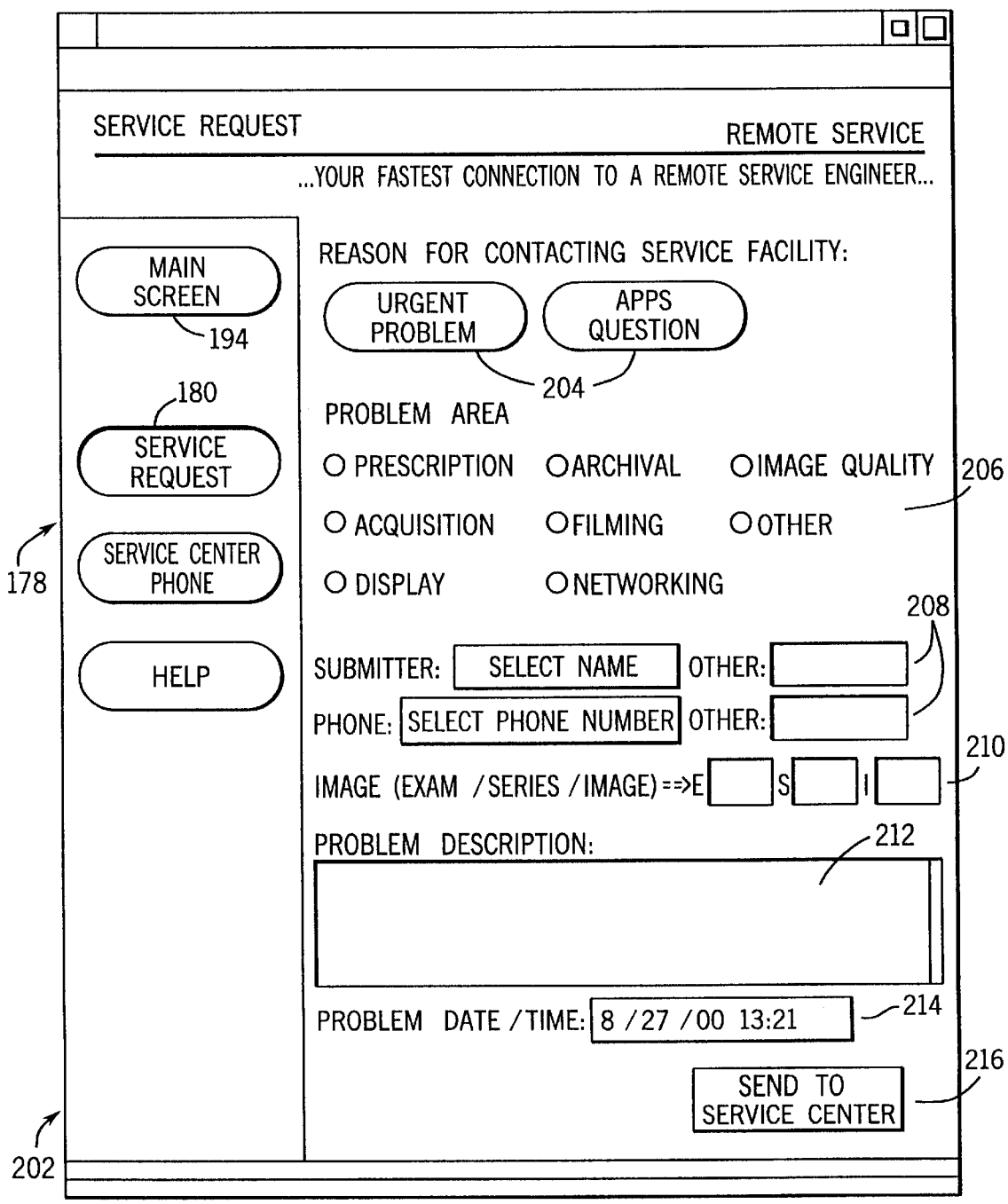
FIG. 8 is an interface page for generating a particular type of service request at the scanner and for conveying the service request to the service facility.

As mentioned above, the uniform graphical user interface facilitates formulation of service requests and enables system designers to permit such service requests in a similar manner across several diagnostic system modalities. FIG. 8 illustrates an exemplary interface page for formulating such service requests. In the page shown in FIG. 8, a "snap shot" or current system state may be captured as the basis for the service request. The service request page would be accessed from the normal operating page at the scanner, through the service request button 180 in the main web page or one of the other web pages. With the system state remaining at its condition just prior to accessing the service request page, image data files, log files, error files, and so forth may be identified, captured, stored and transmitted to the service facility for evaluation of potential problems in the diagnostic system. As will be appreciated by those skilled in the art, the service request therefore enables the user to identify potential imaging system difficulties that may not be apparent in subsequent examinations, or may not reoccur on a predictable basis. It should be noted that the service requests formulated via a page such as that shown in FIG. 8 and described below are not limited to identifying image acquisition or processing problems, or to capturing image files only. Such requests may relate to general or system-specific questions, or may identify data files containing system configuration data, and data indicative of historical operational parameters or events. Such events may include parameter limits exceeded, timeouts, protocol configurations, hardware and software configurations, work queues, and so forth. Similarly, image data identified for evaluation may include both processed, partially processed and raw data from which images are subsequently reconstructed.

The service request page 202, as shown in FIG. 8, includes graphical buttons 204 which permit the user to identify whether the service request is urgent or whether the request entails simply an applications question or non-urgent inquiry. In the illustrated embodiment, a series of interactive selections 206 are available, permitting the user to identify, if possible, the type of problem which may be occurring. Furthermore, a series of identification areas 208 allow the user to insert text to identify both the user, the user's location or telephone number, and other contact information. It should be noted that the server included in the uniform platform already includes unique system identification data which supplements the information input by the user. Such information may be input by a user, or may be supplied automatically by the system. Where the service request involves a specific image or examination sequence, the user may input such identifying data in a series of examination identification areas 210. Where the examination request involves an examination which has just been attempted or is underway, the data required in areas, 210 may be transmitted directly from the modality controller. A further area 212 permits the user to identify or describe the type of service problem being experienced. A date stamp area 214 provides an identification of the date and time of the serviceable problem or question. In appropriate situations, a default time drawn from a system clock may be provided in this area, or the default time may be overridden by the user. Finally, in the embodiment illustrated in FIG. 8, the user may complete and submit the service request by selecting a graphical send button 216. It should also be noted that in the illustrated embodiment, a graphical service center telephone directory button 218 is provided, by which the user may access numbers for immediately contacting the remote service facility.

Figure 9:
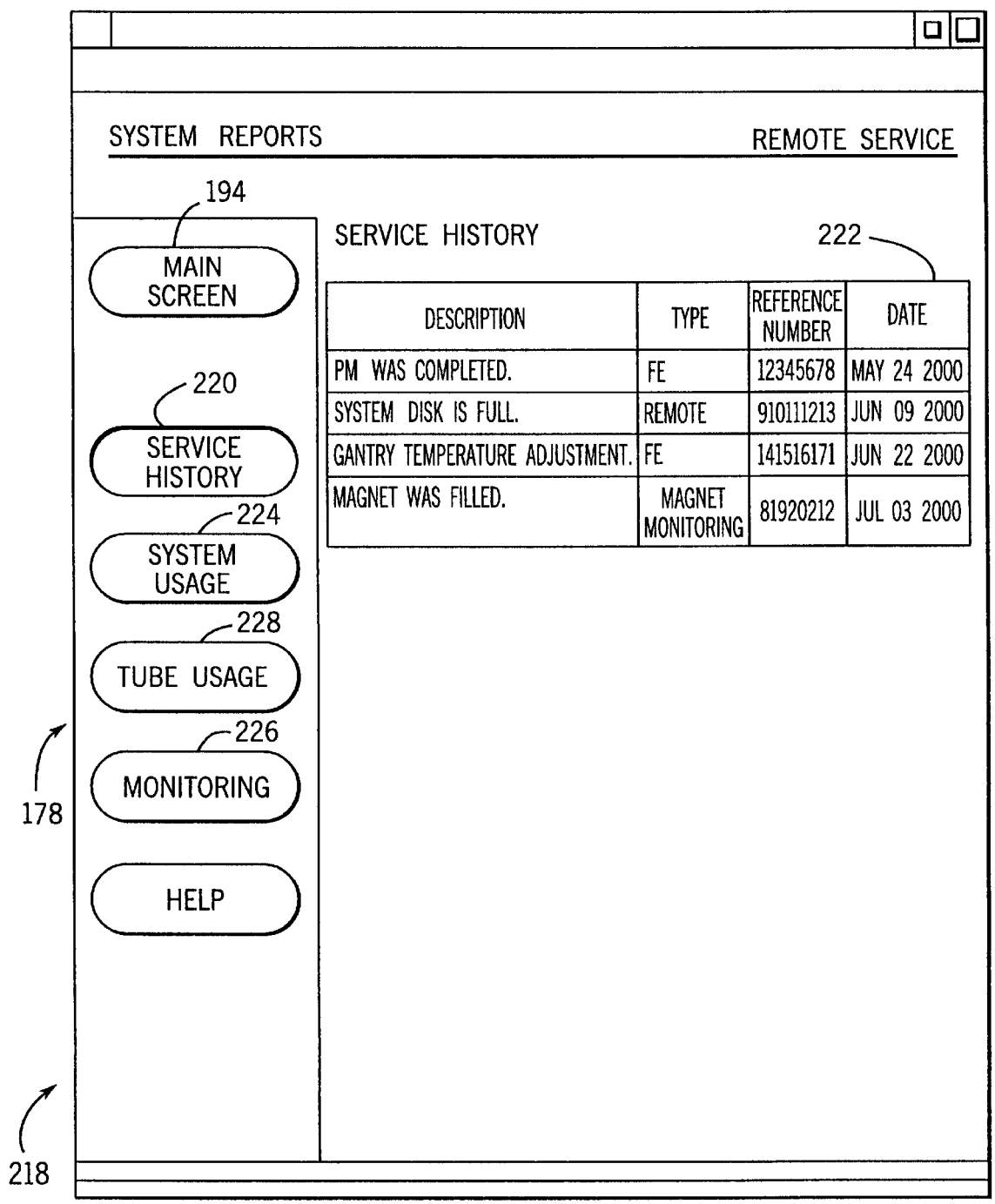
FIG. 9 is an interface page for requesting, compiling and transmitting reports regarding service activities provided by the service facility to the scanner.

FIG. 9 illustrates a further interface page for informing the system operator of the current and past state of service activities, and for transmitting reports to the diagnostic system from the remote service facility. The system reports page 218 includes a series of graphical buttons 178, including certain options which may be provided across a number of modalities, such as a service history button. When the service history button is selected, text appears in a text area 222 which identifies the type of service performed on the diagnostic system, either locally by a service engineer or remotely by the remote service facility. The text may also indicate the nature of the organization performing the service, applicable reference numbers, and the date on which the service was performed. The diagnostic system operator is thereby apprised of all service activities provided to the diagnostic system, and maintains and up-to-date, comprehensive list of the service activities.

Other selections available in the system reports page may include system usage, accessible through a graphical button 224, and monitoring activities accessible through a button 226. It should be noted that the specific information accessed through selection of one of the graphical buttons will be adapted not only for the modality and system type, but for the specific system in which the user interface is installed. Thus, under a system usage page (not shown) a CT system may include data indicative of the performance of an x-ray radiation source, while in an MRI system, the same graphical button may access information on cryogen levels and temperatures. It should also be noted that specific modality or system buttons may be provided, such as a tube usage button 228 in FIG. 9, suitable for x-ray and CT systems. Although such additional interface access devices are configured in individual systems, they are preferably provided in a uniform location and lay out which can be easily learned and used by operations personnel.

Figure 10:
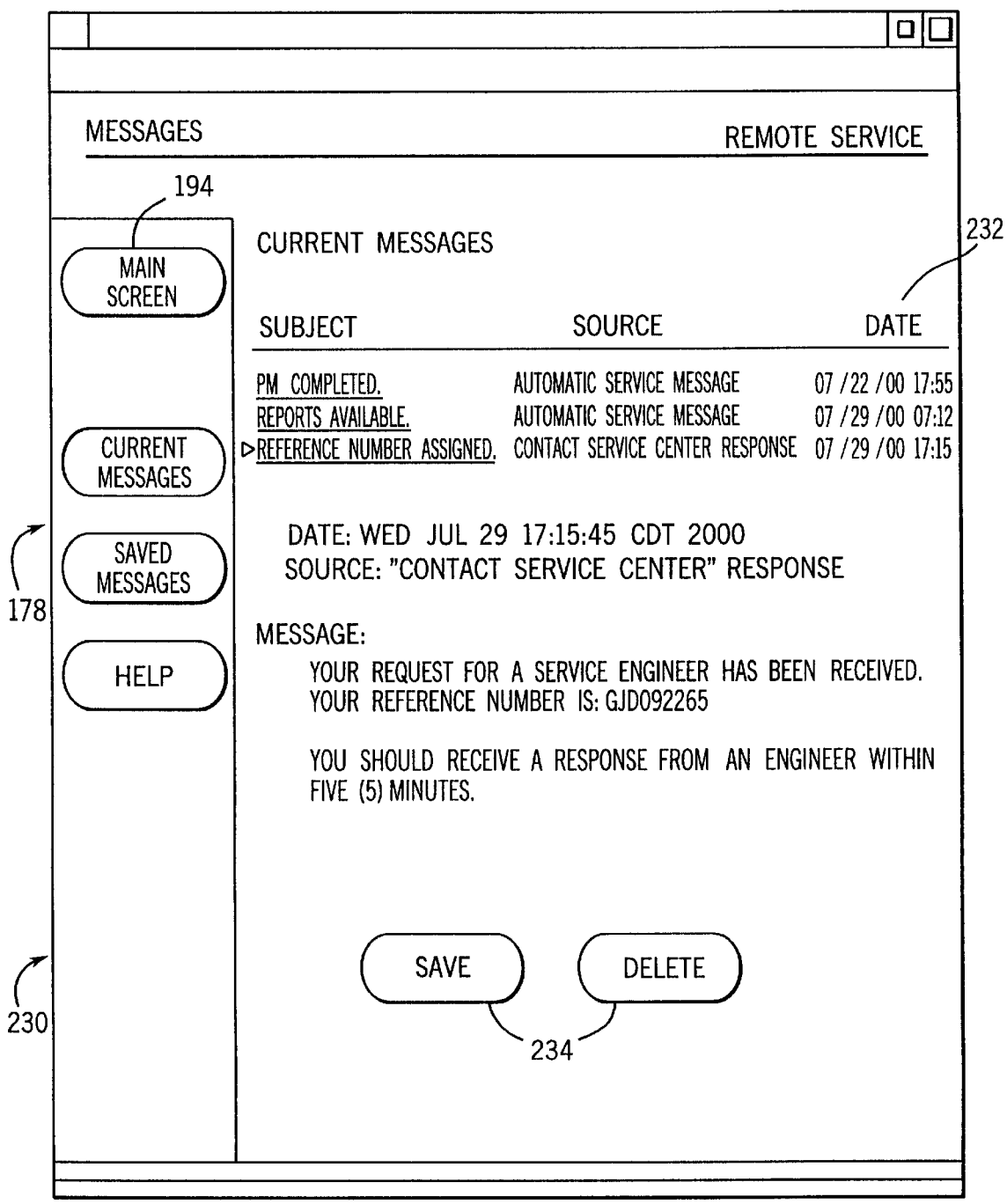
FIG. 10 is an interface page for transmitting and viewing service-related messages from the service facility at the scanner.

FIG. 10 illustrates a messages page for the uniform platform and graphical user interface. Messages page 230 is accessible through the main page shown in FIG. 6. Upon accessing the messages page, the system user is provided with information on service and other messages received by the diagnostic system via a network connection. A pair of graphical buttons are provided for selecting either current messages or saved messages received by the system. Upon selection of either the current or saved messages button, the user is provided with a list of messages in a text area 232, identifying the subject of the message, the originator, and the date received. The body of the message, and graphical symbols indicating possible attachments (none shown) are also provided in the text area 232. The user may select a particular message for viewing by selection of the entire or a portion of the text defined in the tabulated message list.

As described more fully below, when a service request is composed and transmitted to the remote service center, an acknowledgment message is generated and returned to the diagnostic system, indicating that the service request has been received and is being processed. Moreover, where reports are generated, based either on a service request or on an automatic or a periodic basis, the availability of such reports may be flagged through the message page. Both the message and the report may then be accessed by appropriate selection of the message title in the tabulated list. The user may save or delete each message by selection of an appropriate save or delete graphical button 234.

Figure 11:
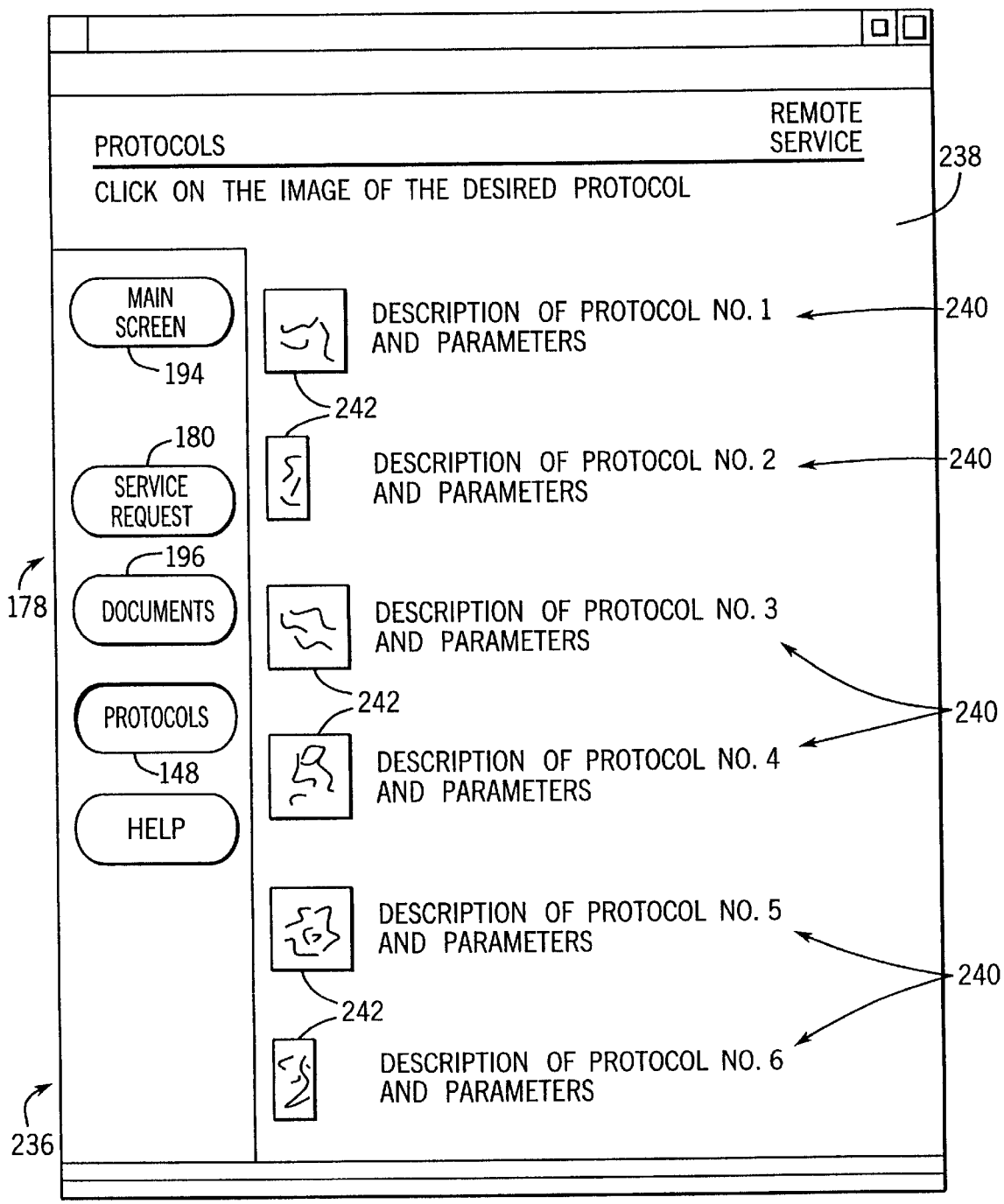
FIG. 11 is an interface page including descriptions of software routines, such as imaging protocols, at the diagnostic system scanner which are installed at the scanner or available from a service facility or library.

As illustrated in FIG. 11, further interface pages may be provided for listing available software, uploading such software into the particular modality controller, or downloading the software from a library or service facility. In the embodiment illustrated in FIG. 11, such software includes a series of examination or imaging protocols. As will be appreciated by those skilled in the art, such protocols define configuration parameters for specific examination sequences. In general, however, as used herein, the term "protocols" generally refers to instructions or parameters for acquiring, manipulating, displaying, archiving or managing medical diagnostic data. The protocols are specifically adapted for the modality of the diagnostic system, and may be further adapted for specific system types and capabilities. In presently preferred configurations, the protocols may be stored locally at the particular diagnostic system, or may be available at the diagnostic system via a variety of transfer options or memory support devices, such as CD ROM storage discs. It should be noted, however, that interface pages such as that shown in FIG. 11, and the processing described below, are not limited to transfer of protocols, but may include transfer of a wide range of programs.

The available software routines are listed and described briefly in the user-viewable page. In FIG. 11, the protocol screen 236 lists a series of imaging protocols within a text area 238. For each protocol provided in the listing, a brief description of the protocol and its configuration parameters is provided as indicated at reference numeral 240, as is a condensed image or thumbnail sketch of the type of image available through application of the protocol, as indicated at reference numeral 242. Additional protocols may be made available by paging down the list in a conventional manner. Also, in a preferred embodiment, protocols presented in a menu may be sorted, such as by anatomy, imaging or acquisition technique, physiological condition or pathology, and so forth. As described in greater detail below, in a preferred embodiment, not only are the protocols displayed for reference purposes at the diagnostic system, but new or additional protocols may be added to the listing from time to time, such as by downloading from the service facility. Moreover, certain of the protocols may be made available on a fee-per-use, one-time payment, or a license basis. Furthermore, the user may upload examination configurations by selecting the thumbnail image or text associated with a particular protocol. Thus, the uniform user interface and platform facilitate not only viewing and listing such routines and protocols, but assist in the examination configurations themselves.

Figure 12:
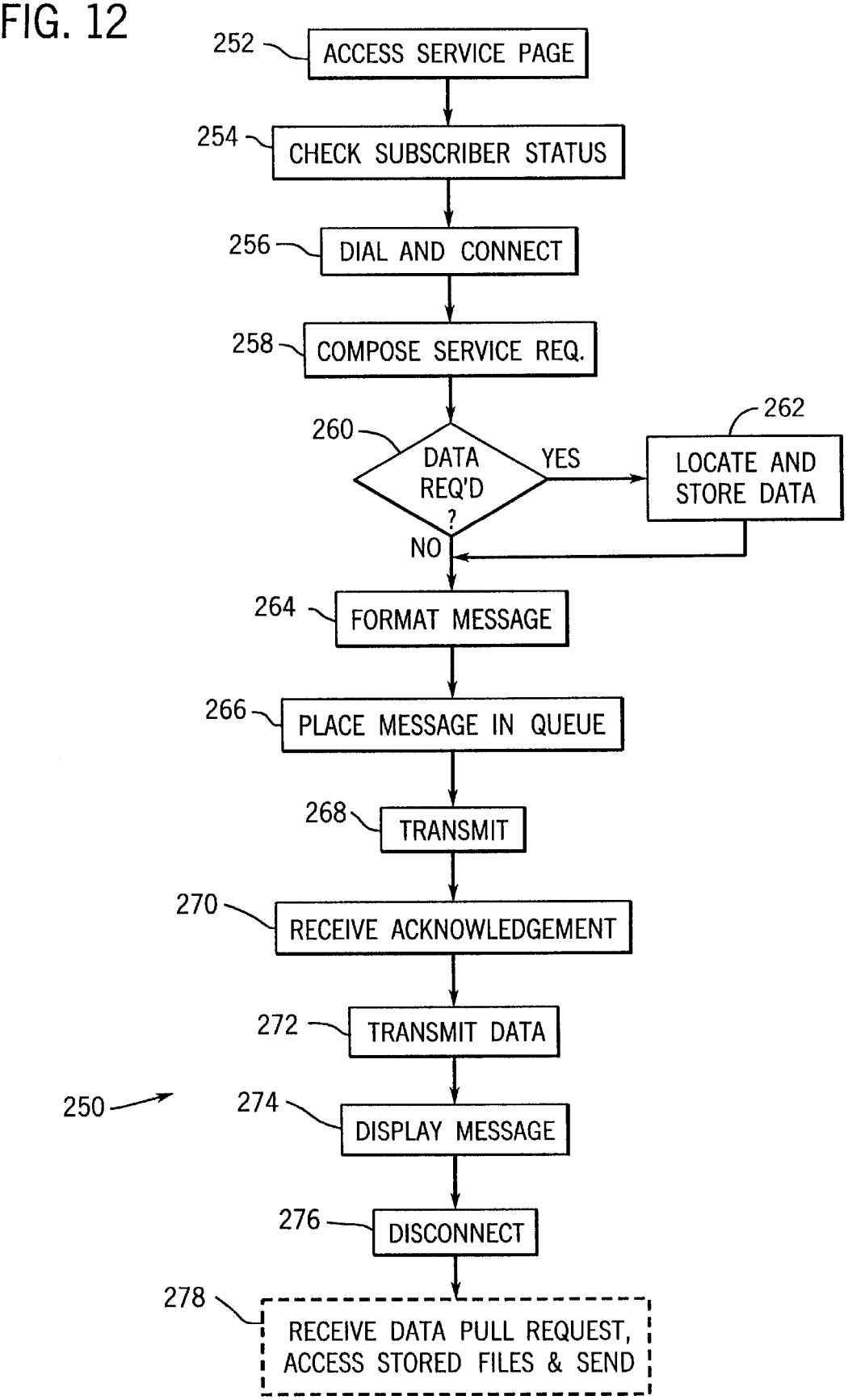
FIG. 12 is a flow chart illustrating exemplary logic implemented by the diagnostic systems for requesting one type of analysis and service from a remote service facility.

FIGS. 12 through 16 illustrate exemplary control logic implemented by the functional components described above at the diagnostic systems, the service facility, and remote field service units. In particular, FIG. 12 illustrates exemplary logic for composing and transmitting a service request via the graphical user interface and uniform platform. The control logic, indicated generally by reference numeral 250, begins at step 252 wherein a service page is accessed from a normal operating page at the diagnostic system or at a management station. The logical steps illustrated in FIG. 12 are particularly adapted for composing service requests based on specific instances of malfunctions or specific questions on examination sequences. Thus, at step 252 a service request page such as that shown in FIG. 8 is accessed. At step 254 the diagnostic system may verify a subscriber status required for the requested service. In particular, the various service requests may be categorized by type, and associated with specific contract types, subscriber services, licenses, and so forth. Such subscriber data will be stored in a license module such as module 114 shown in FIG. 3. Where the service requests are freely made by the scanner, this step may be eliminated. However, where specific service subscriptions are required, a comparison is made at step 254 between the required contractual arrangement or subscriber license and the similar information on file for the diagnostic system. At step 256 in FIG. 12, the diagnostic system connectivity module dials and connects the diagnostic system to the service facility. At step 258 the service request is composed, such as by selecting or inputting the question description, user identification, problem description and other information as described above with respect to FIG. 8.

At step 260, the diagnostic system server 130 (see FIG. 3) determines the type and location of data that may be required for addressing the service request. For example, for service requests regarding imaging sequences, acquired image data files may be identified, along with scanner log files, error files, and so forth. More particularly, the data identified (and later transmitted if required) may include both raw or processed image data, software configuration information, systems data (e.g. hardware and software identification and configuration), and so forth. Certain of the data may be specific to the modality of the system (such as data in a DICOM format), and may be defined by modality through adaptation of the uniform platform via the modality interface components. Where such data is required for properly addressing the service request, the data files are located as indicated at step 262. The files may be backed up or stored from the modality-specific circuitry through the intermediary of adapter modules, such as adapter module 116 (see FIG. 3). These steps in the exemplary logic therefore permit the user to configure a service request which effectively captures a state of the diagnostic system which gave rise to the service request. The request may be thereby linked to the specific problem for which service is needed.

At step 264 a message is formatted based upon the service request. The message formatting will typically include identification of the diagnostic system, a facility in which the system is located, and so forth. It should be noted that in the preferred embodiment, the service request and the message is stripped of information relating to specific patient identifications. Other data, such as financial or account information may be included with the message or may similarly be stripped from the request. Where the requested service is permitted by the subscriber arrangement, the logic proceeds to step 266 where the request is placed in a message queue at the diagnostic system. If the subscription arrangement does not permit the specific type of request, the logic may produce a message notifying the system user of this fact, may proceed based upon an exception to the subscriber arrangements, or both.

At step 268 the service request message is transmitted. The service facility receives the service request and processes the request as summarized below. In the preferred embodiment a request acknowledgment signal is immediately transmitted by the service facility back to the diagnostic system and is received by the diagnostic system at step 270. The diagnostic system operator is thereby immediately provided with feedback on the status of the service request, including information relating to a reference code and estimated handling time. At step 272 a portion or all of the data files may be transmitted by the diagnostic system to the service facility. Alternatively, transmission of all or some of the data files may be delayed until a subsequent service connection session. At step 274, the acknowledgment message is posted on the message page of the graphical user interface, and a notification that the message has been received may be posted on the interface page which is currently being viewed at the diagnostic system. At step 276 the diagnostic system may disconnect from the service facility. Alternatively, additional messages, service requests, and so forth may be transmitted, or other remote activities may be performed at this stage. When certain of the data required to address the service request is not transmitted immediately, the service facility may recontact the medical diagnostic system at a subsequent time. As indicated at step 278, a data file pull request may be transmitted by the service facility, and, in response to the request, the platform at the diagnostic system will access the required files and transmit the data to the service facility for analysis.

Figure 13:
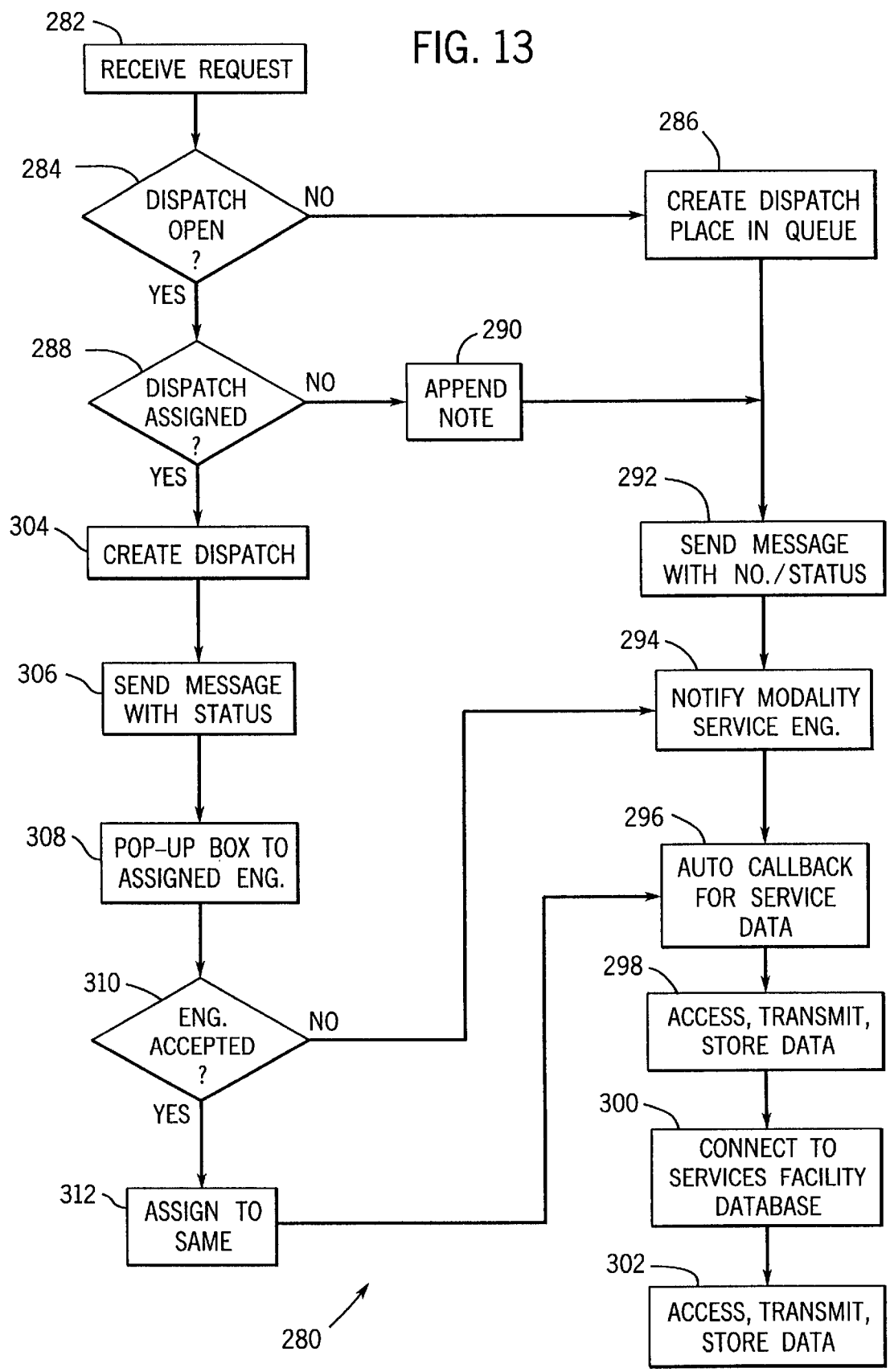
FIG. 13 is a flow chart illustrating exemplary logic in handling such service requests by the service facility.

FIG. 13 illustrates steps in exemplary control logic for addressing the service request at the remote service facility. This request handling logic, indicated generally by reference numeral 280, begins with receipt of the request as indicated at step 282. The request is received via the network connectivity modules of the service facility and is handled by the service center processing system including the HTTP server 140 and the analysis server 142 (see FIG. 4). In addition to the steps illustrated in FIG. 13, the service facility servers will verify license or other subscriber data for the diagnostic system or site requesting the service as described more fully below with reference to FIG. 14.

Upon receipt of the service request and subscriber clearance, the service facility processing system determines, at step 284, whether a service dispatch has been opened. As used herein, the term "dispatch" refers generally to a service request tracking or handling technique, such as for referencing a service request or identifying the service request or response at a later time. The logical steps executed at step 284 may include comparison of the origin and nature of the service request with service requests already received and being handled by the service facility. If, through this comparison, it is determined that no dispatch has been opened for the particular request, a dispatch is created at step 286 and the service request is placed in a handling queue. If a dispatch has already been created, it is determined at step 288 whether the dispatch has been assigned to a service facility engineer for handling. If the dispatch has not yet been assigned, a note is appended to the dispatch at step 290 indicating that the service request has been repeated. From either step 284 or step 290, a message is generated at step 292 including the reference number of the dispatch in the service facility or an update on the status of the preexisting dispatch. This message is then transmitted to the requesting diagnostic system or site and is received and posted by the site as described above with respect to FIG. 12.

Following transmission of the acknowledgment message at step 292, a modality service engineer is notified of the service request at step 294. Because in the present technique the service facility may provide interactive service to a variety of system modalities, at step 294 a service engineer, typically staffing a workstation 86 (see FIG. 4) in the service facility is assigned service requests according to the particular modality of the diagnostic system. It should be noted, however, that the modality service engineer assigned the service request may be remote from the service facility, and may be a field service engineer accessible through a field service unit 24 (see FIGS. 1 and 2). At this point in the control logic, the service facility may be disconnected from the requesting diagnostic system.

Where the service request requires data, such as image data files, log files, and so forth, from the diagnostic system, this data may be transmitted along with the request. However, where voluminous files are needed, or where files are identified by the service facility or by a service engineer subsequent to receipt of the request, the diagnostic system may be recontacted by the service facility as indicated at step 296 to locate and transmit the needed data. At step 298 the data is accessed, transmitted and stored. The steps involved in recontacting the medical diagnostic system and transmitting the needed data files may require prompting of operations personnel for the input of specific information, or may be essentially transparent to the diagnostic systems operations personnel. Thus, the service facility server or servers may contact the diagnostic system server directly to access and transmit the needed data without intervention from the operations personnel at the diagnostic system facility.

Depending upon the nature of the service request, the service facility engineer will perform analysis of the service issues and recontact the diagnostic system either in person, by telephone, or directly through the network connection and user interface. For particular service requests, the service facility database may be utilized as indicated at step 300 in FIG. 13. Such databases will be called into play in reviewing or updating service history for the particular diagnostic system or site, as well as for referring to configuration parameters, operating parameters, reference values, and so forth for the particular modality and system type. The databases accessed at step 300 may also include information relating to populations of diagnostic systems. Such information may be used by the service facility for comparison purposes, predicting possible future service needs, predicting component failure or degradation, and so forth. Moreover, the access to the databases at step 300 may include access to new or updated routines, protocols, instructional documentation and courses, schedules for training, and so forth. Where such information is located for the diagnostic system modality and type, the data may be included in messages formulated by the service facility and retransmitted to the diagnostic system. At step 302 the database information is therefore accessed, transmitted and stored for responding to the service request.

Returning to step 288, if at this step it is determined that a dispatch has been assigned, a further dispatch may be created at step 304. A message, including the update regarding the dispatch, is formulated and sent at step 306 to inform the diagnostic system operations personnel of the status of the service request. A "pop up" box message is then addressed to the assigned service engineer at step 308. At step 310 the processing system determines whether the assigned engineer has accepted the dispatch. If no engineer accepts the dispatch or a predetermined interval lapses following display of the notification at step 308, the logic proceeds to step 294 wherein a modality service engineer is notified of the service request. Subsequent logic follows step 294 as described above. If upon displaying the notice at step 308 a particular service engineer accepts the service request, the request is assigned to the engineer at step 312 and the logic may proceed to step 296 as described above.

In general, substantive responses to service requests will vary depending upon the tenor of the request. For example, the response may include suggestions for operating the diagnostic system or a medical institution in which the system is installed. Such information may provide "best practices" type information for the particular system type or modality, as well as instructional information on user or care for the system. The information may also include alerts, such as for anticipated service needs, scheduled or available training sessions and so forth. As described below, the response may further include programs or protocols or reports of system operation. It should be noted that the same type of information may be provided to the diagnostic system at the initiation of a remote service facility as part of a service program or otherwise.

Figure 14:
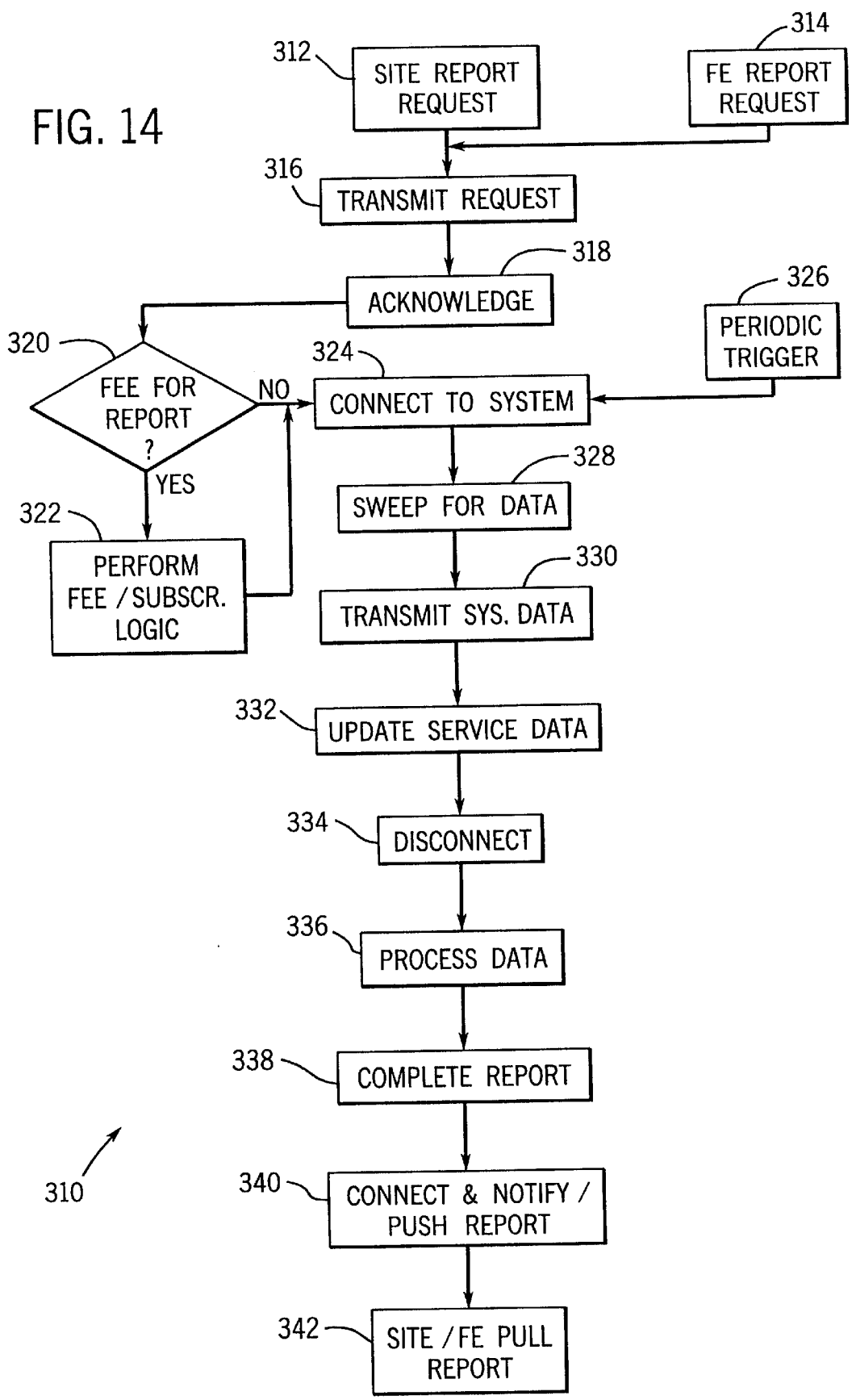
FIG. 14 is a flow chart illustrating exemplary logic for reporting service activities, updates, alerts, and so forth from the service facility to a diagnostic system.

FIG. 14 illustrates steps in exemplary control logic executed by the service system for requesting, compiling and transmitting reports relating to service activities and operation of the medical diagnostic systems. The control logic, indicated generally by reference numeral 310, may begin in one of several manners, depending upon whether the report is being generated automatically, or upon request by a particular diagnostic system, or by a field engineer. Where the report is specifically requested by a diagnostic system, the report request is produced at step 312 by the system operator or manager via the uniform graphical user interface described above. Various types of reports may be produced, including reports relating to recent or historical service activities, reports of the state of the diagnostic system, including numbers and types of examinations performed, errors or problems encountered, anticipated service needs, and so forth. For example, in x-ray and CT modalities, reports may relate to the operational status of the x-ray tubes, while in MRI systems, reports may include data relating to cryogen levels and temperatures. Moreover, reports may be requested for financial, subscription, or other management functions, including listings of current license subscriptions, accumulated fees for specific accounts (e.g. resulting from pay-per-use or one-time fee arrangements), and so forth. Similar reports may be requested by field service engineers and technicians as indicated at step 314.

At step 316 the report request is transmitted to the service facility. The report request will typically be transmitted in the form of a service request message as described above with reference to FIG. 12. At step 318 the transmitted request is acknowledged by a return acknowledgment message from the service facility, providing an indication of receipt and confirmation of handling of the report.

Certain of the reports available through the system may be provided free of charge, or based upon specific subscription types, or for a fee. Thus, as shown in FIG. 14 at step 320, following acknowledgment of receipt of the report request, the service facility processing system may evaluate the request to determine whether a fee is applicable. If a fee is associated with the report requested by the diagnostic system user, a fee/subscription routine is performed as indicated at step 322. Exemplary control logic involved in the fee/subscription routine is described below with reference to FIG. 15.

Following either step 320 or step 322, the service facility is contacted via a network connection as indicated at step 324. It should be noted that while the fee verification steps indicated at steps 320 and 322 may be performed in the medical diagnostic system, similar steps may be performed in the service facility following step 324, or between the diagnostic system and the service facility interactively, depending upon the particular fee arrangement and the data required for authorization of the fee structure. As indicated above, the reports generated by the service system may result from triggering events other than a specific request. In particular, certain reports may be generated on a periodic basis, such as weekly or monthly, and the service facility or the medical diagnostic system may generate a prompt for a report based upon a preestablished calendar or routine. Thus, as indicated at step 326, a periodic trigger may give rise to either the medical diagnostic system contacting the service facility, or vice-versa.

Once the diagnostic system and service facility are linked, the service facility may sweep the diagnostic system for data required for the desired report as indicated at step 328. As used herein, the term "sweep" refers generally to a process of connecting system components, such as via a network connection, identifying desired data, and transmitting the data, either in an "upload" or a "download" scenario, depending upon the nature of the data and its use in servicing a system. Such sweeps may occur on regularly scheduled bases, at desired times (e.g., at off-peak utilization times) or on demand by a system user or a system application. The system data may be stored in specific data files which are accessed either through intervention of a service engineer, or automatically by the service facility processing system. Once the data is accessed, it is transmitted to the service facility as indicated at step 330. At step 332 the service data records for the particular diagnostic system, as well as records kept for specific populations of similar diagnostic systems is updated as indicated at step 332. Subsequently, the service facility may disconnect from the diagnostic system as indicated at step 334. In situations in which no further data from the diagnostic system is needed for generation of the requested report, the steps of data collection and transmission may be eliminated. Moreover, the service facility may perform periodic data sweeps of subscribing systems without immediately generating a report through the subsequent logical steps.

Where a report is to be generated based upon the acquired and historical data, the data is processed as indicated at step 336. As will be appreciated by those skilled in the art, the specific processing performed at this step may vary widely depending upon the nature of the diagnostic system, the data being processed, the type of report being generated, and so forth. For example, the data processing may include statistical analysis of the acquired data, categorization of data, as well as failure prediction analyses based upon the data, and so forth. The processed data is then compiled into the desired report as indicated at step 338. The report may include tabulated presentations, but may also include compilations of data into graphical formats, such as charts, graphs, and so forth, which may be accessible through a series of interactive pages viewable by the diagnostic system user via the local browser.

At step 340 connection is reestablished with the diagnostic system and a notification of the availability of the report is transmitted. Several scenarios are available for transmission of the requested reports. As indicated at step 340, the requested report may be transmitted with the notification message in a "push" scenario. In general, such techniques will append the report to a notification message which is transmitted and displayed at the diagnostic system. The user may then access the report by appropriately selecting the message or an icon or text associated with the message. Where desired, however, reports may be compiled and a notification message provided at step 340, requiring the diagnostic system or the site to recontact the service facility and to "pull" the report as indicated at step 342. Where the report was requested by a field service engineer, similar steps are performed for transmitting the desired report to the field service engineer, or for permitting the field service engineer to pull the report based on a notification message. Moreover, where reports are requested by or transmitted to specific diagnostic systems or sites, the field service engineer may be notified of the request or the report at the same time as the report is transmitted to the diagnostic system. It should be noted that, when desired, a report maybe stored at a location remote from the diagnostic system, and nevertheless be viewed at the diagnostic system, such as via a browser interface (e.g. as a series of web pages). Moreover, where desired, a report may be requested by the system to be delivered via facsimile. In such cases, the report is requested and compiled as described above, then transmitted via facsimile to the institution in which the system is installed or, in appropriate applications, directly to the requesting system.

Figure 15:
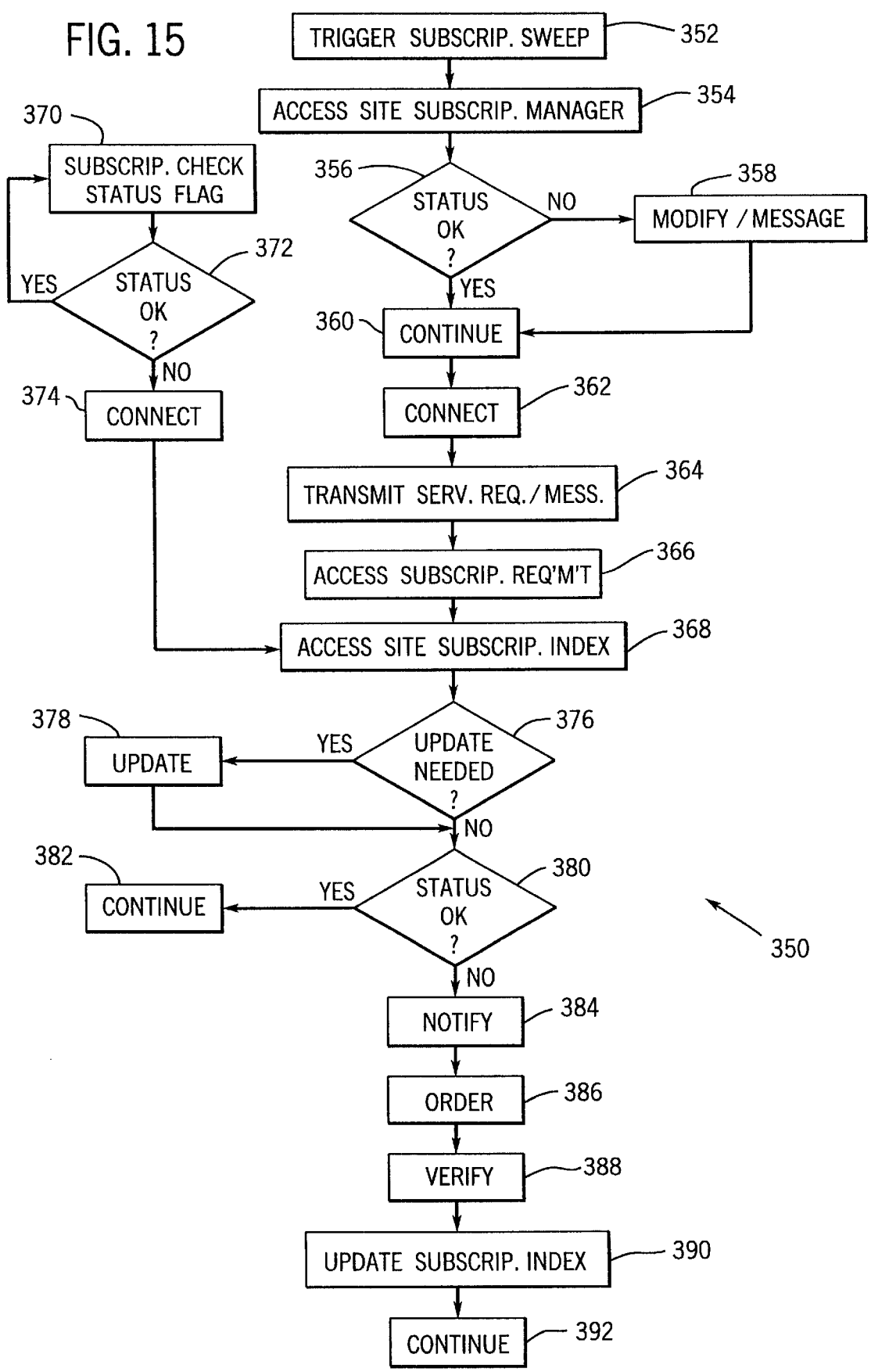
FIG. 15 is a flow chart illustrating exemplary logic for verifying and controlling financial and management arrangements between the service facility and the diagnostic systems, such as licensing arrangements, subscription arrangements, pay-per-use arrangements, and so forth; and, FIG. 16 is a flow chart illustrating exemplary control logic for accessing diagnostic protocols both from a local storage source at the diagnostic system, as well as from a remote library.

FIG. 15 illustrates exemplary control logic for verifying and controlling financial and management arrangements between the service facility and diagnostic systems. As mentioned above, the logic illustrated in FIG. 15, designated generally by the reference numeral 350, may be triggered in a variety of manners. For example, verification of license or subscriber status may be triggered each time the service application is accessed at the medical diagnostic system. Similar triggering may occur upon request for specific types of service at the remote service facility. Moreover, both the diagnostic system and the remote service facility may include routines designed to trigger an alert upon expiration or anticipated expiration of a dated subscription. Furthermore, subscription or license verifications may relate to all or a part of the platform or configuration of the diagnostic system, such as particular programs, applications, protocols and so forth. In a presently preferred embodiment, other security checks may be performed in addition to such subscription verifications to prevent tampering. For example, when the service platform is started, a coded check sum for files is compared to a reference (e.g., created upon installation or subsequent updating) If the comparison reveals possible tampering, a note is made in a log file which can be monitored remotely.

In the presently contemplated embodiment, several types of fee or financial management arrangements may be provided in parallel. Firstly, a service subscription may exist for certain levels of service. The service subscription may time out periodically or may be permanent, such as lifetime or non-expiring warranty service. Secondly, certain of the services provided remotely may be offered on a pay-per-use basis. In such cases, the logic of FIG. 15, or other financial management logic may be triggered upon generation of a service request, receipt of the service request, or fulfillment of a service order. Finally, certain services or service data may be provided based on a purchase arrangement, in which the diagnostic system operator orders service or data and the associated fee is invoiced or debited to the diagnostic system account. Such arrangements may be employed, for example, for the transfer of new examination protocols, software, and so forth.

The logic of FIG. 15 begins at step 352 with the triggering of a subscription check. As used herein, the term subscription should-be understood to encompass both ongoing and periodically expiring licenses, pay-per-use arrangements, purchase arrangements, and other service and distribution arrangements. As illustrated in FIG. 15, step 352 will generally occur at the diagnostic system. At step 354 a subscription manager module contained within the license module 114 of the diagnostic system is accessed. The subscription manager module will include data relating to specific applications or services to which the diagnostic system holds rights or subscriptions, as well as data relating to expiration dates, levels of service, system identification, and so forth. At step 356, the system determines whether the status of the various subscriptions is up-to-date or whether certain of the subscriptions may be expired. If any such problems with the service subscriptions is detected at step 356, operation of the service platform or interface may be modified as indicated at step 358. Rather, or in addition to such modification in the service platform presentation or operation, a message may be generated and displayed at the diagnostic system indicating the need to contact a field service engineer or the service facility, or to update the subscription. Following step 358, the service activities may continue as indicated at step 360. Step 360 is also reached where the status of the subscriptions checked at step 356 are found to conform to the needed status for the service activities desired by the user.

Following the local verification of the subscription status, the diagnostic system may be connected to the service facility as indicated at step 362. At step 364 any service requests or messages composed at the diagnostic system may be transmitted to the service facility as described above. Based upon such service requests and messages, a further subscription review may be performed in conjunction with the service facility. In particular, as indicated at step 366, certain of the service or data requests transmitted from the diagnostic system may require payment or authorization of a fee. Such requirements are identified at step 366. At step 368 a site subscription index maintained at the service facility is accessed. The site subscription index will typically be stored in a license database 146 (see FIG. 4A). The index includes up-to-date information regarding current subscriptions, account data, system identification, authorization data, and so forth, for the specific diagnostic system and the services to which the diagnostic system either holds rights or licenses. The subscription index information is used by the service facility to update the data at the diagnostic system, as well as to authorize the requested service, or to perform accounting functions for debiting appropriate accounts for paid services. Where desired, subscription authorizations may also be automated between the service facility and diagnostic systems or medical institutions.

As indicated above, certain financial arrangements may be verified periodically either at the diagnostic system or by the service facility processing system. Step 370 in FIG. 15 indicates a periodic subscription check or status flag which may occur based upon such periodic license checking routines. When a periodic license check is triggered, the status of applicable licenses is verified at step 372. If the statuses are current (e.g. no expired license flags are identified), normal operation may continue. However, where the status check indicates that certain subscriptions have expired or will expire, the specific diagnostic system involved may be contacted by connecting to the service facility network as indicated at step 374. Following the connection, the site subscription index is again accessed at step 368 as summarized above. The site subscription index accessed at step 368 provides a basis for verifying and updating corresponding status data with the diagnostic system. Thus, at step 376, the subscription index is compared to similar subscription information stored at the diagnostic system, and it is determined whether an update is required. In general, it is presently contemplated that the master version of such information will be stored at the service facility. In practice, portions of the indices or subscription files may be compared, or data derived from the indices or files may be compared for this purpose. Moreover, security devices may be included in the system to prevent unauthorized modification of the subscription data at the diagnostic system. Thus, if at step 376 the diagnostic system data is found not to conform to the information at the service facility, it is assumed that the diagnostic system is to be updated, and such updates are performed as indicated at step 378. Following either step 376 or 378, the status of the particular subscriptions are verified at step 380. This status verification may include, again, comparison of the current system subscriptions with the subscriptions necessary for the requested service. Moreover, the status check may verify whether the requested service is a pay-per-use service, a one-time fee service, and so forth. If the current subscription or financial arrangement is found to be in place at step 380, the system may continue with the handling of the service request as indicated at step 382.

If at step 380 updating or fee authorization is required, a notification to this effect may be generated as indicated at step 384. Such notification will generally take the form of a message transmitted from the service facility to the diagnostic system as described above. Moreover, the notification may include one or more interactive pages for ordering or authorizing the required fee arrangement. Upon completion of such information or authorizations, the requested service may be ordered as indicated at step 386. Where the authorization is not received, the request handling may be aborted at this stage. Upon transmission and receipt of the order or authorization data from the diagnostic system to the service facility, the service facility may perform verification routines as indicated at step 388, such as by comparing authorization codes with established codes stored within the subscription index. The subscription index is updated at step 390. Such updating will typically include indication of new expiration or renewal dates, addition of the authorization or fee arrangement to service history databases, and addition of the requested and authorized fees to accounting databases for debiting or invoicing purposes. Finally, once the required financial arrangement is established or verified, the handling of the service request may continue as indicated at step 392.

FIG. 16 illustrates exemplary logical steps for transmitting service and diagnostic programs from the service facility to diagnostic systems. As mentioned above, such programs may include new or revised examination sequences, protocols, and the like. While such protocols may be distributed on supports such as CD ROM discs, they may alternatively be supplied via the network connection established between the service facility and the diagnostic systems. As used herein, the term program also refers to prerecorded or live transmissions such as video and audio transmissions employed by the facilities housing the diagnostic systems for personnel training purposes and the like. Such programs may be stored for distribution over a network as scheduled by the diagnostic system personnel, or may be prescheduled, such as through a preestablished training program or periodic training sessions.

The logical steps depicted in FIG. 16, denoted generally by the reference numeral 400, begin with definition of the program at step 402. In general, and in particular for diagnostic system protocols, such programs will be defined specifically for the particular modality of the diagnostic systems, and, where appropriate with additional specificity according to the system type, model, and so forth. Such program content may be defined by the service facility or by other content providers. At step 404, the program is stored, such as in a database 156 or other storage device accessible to the service facility (see FIG. 4).

Several scenarios are presently envisioned for distribution of the programs via the service system described above. In particular, such programs may be distributed at the initiation of the service facility, or upon request by the diagnostic system. Where the service facility makes such programs available, the programs may be distributed via a "push" or "pull" scenario. In the former case, the programs are downloaded at the initiation of the service facility as described below. In the latter case, the diagnostic system is notified of the availability of the program, and may download or upgrade the system at will by recontacting the service facility. In either case, notification is displayed at the diagnostic system through the interactive interface to inform the operations personnel of the availability or the presence of the program. For example, in the case of examination protocols, notification may be provided via the protocol page illustrated in FIG. 11, with the new examination protocol either stored locally at the diagnostic system, or available upon request from the service facility, or from a library or other resource to which the service facility or diagnostic system browser may connect the diagnostic system. Such connections may be implemented through conventional Uniform Resource Locator (URL) links.

At step 406 of FIG. 16, the service facility processing system determines whether the program is to be distributed via a "push" or "pull" scenario. If the program is to be downloaded directly via a "push" scenario, subscription records are obtained from the service facility databases at step 408 to determine the present status of service subscriptions, and to compose a list of subscribing diagnostic systems to which the program is applicable and should be distributed. At step 410 one or more messages to such systems are composed. Where programs are available or may be used by various system types or models, several messages may be composed at step 410 specifically adapted to the variations between the system types. Returning to step 406, where a "pull" scenario is to be employed for the program distribution, the subscription records of the service facility are again consulted at step 412 to develop a subscriber list to which the program should be made available. In general, such pull lists may be compiled where specific programs, including training sessions, protocols, and so forth, will be made available on a pay-per-use, one-time payment basis, or similar arrangements. At step 414, one or more messages are composed for the subscriber list generated at step 412. From either step 410 or 414, the service facility may proceed to contact the diagnostic systems and to establish the network connection described above, as indicated at step 416. At step 418 a message notifying the diagnostic system personnel of the existence and availability of the program is transmitted to the connected diagnostic system. Where the "push" distribution scenario is employed, step 418 may include loading of the program on the diagnostic system without requiring the intervention of the system operations personnel, but including notification of the presence of the new program.

As mentioned above, in lieu of the service facility-initiated distribution mechanism, the diagnostic system itself may originate program requests. Thus, as indicated at step 420, such request may be formulated, typically as a service request as described above. At step 422 a subscription requirement associated with the program may be checked, if such a requirement is stored locally at the diagnostic system. Where such a requirement is stored at the diagnostic system, the subscription manager module of the system may be accessed as indicated at step 424, and the requirement and status compared as indicated at step 426. If the comparison made at step 426 determines that the program requires a subscription status or other arrangement or authorization which is not currently held by the diagnostic system, notification to the user is provided as indicated at step 428. From either step 426 or step 428, the system may continue with the program request procedure, or other interactive service procedures as noted at step 430. As mentioned above, such subscriptions, including for programs and protocols, may be of set to expire at particular times or after fixed durations. In addition to the subscription verification, comparisons made at step 426 may include verifications of hardware or software configurations to ensure that particular programs or protocols are suitable for the requesting system.

Where the foregoing logic allows the diagnostic system to proceed with ordering the requested program, a connection is established at step 432 with the service facility. At step 434 the program request is transmitted, such as in the same manner as other service requests. At step 436 the service facility processing system may access the site subscription index, in much the same manner as described above with respect to the steps of FIG. 15 (see, e.g., step 368). The subscription index data is then compared with the similar data from the diagnostic system, as well as with requirements imposed by the particular program being requested. At step 438 this status is compared, and if additional subscriptions, data, or fee authorization is required, notification is provided via a return message to the diagnostic system as indicated at step 440. Where the foregoing steps permit transmission of the program according to the request, a message indicating its availability is transmitted at step 418 as described above. Again, the message may be accompanied with the program data in accordance with a "push" scenario or may be transmitted at a subsequent time.

Where the program data is transmitted at step 418, an installation step follows as shown at step 442. The installation step may include expanding of program files, modification of resident files at the diagnostic system, enabling of software applications, and so forth. Where the requested program includes audio or video training sessions, other steps may be included at this installation stage, such as routing the requested program to a predetermined location or locations. In addition to the installation step the subscription data, both at the diagnostic system and the service facility, is updated at step 444. For program distribution on such fee arrangements as pay-per-use, one-time payment, or expanded fee-based subscription services is provided, the updating performed at step 444 may include both updating of subscription manager and subscription index files, as well as updating of accounting files for debiting or invoicing the subscribers account. At step 446 the service facility may be disconnected from the diagnostic system.

As noted above, the interactive nature of the program distribution permits notification of the diagnostic system user by means of visual or auditory messages at the diagnostic system. Thus, as indicated at step 448, a message is posted at the diagnostic system, indicating the availability or transfer of the program at the initiation of the service facility or in response to a request from the diagnostic system. Where the program is made available, but is not immediately transferred to the diagnostic system, a delayed transmission or subscriber "pull" step may be included as indicated at step 450. The logic involved in such delayed transmission will typically follow the foregoing steps, including establishing a network connection between the diagnostic system and the service facility, verification of subscriber status, and transmission of the program. Once the program has been transmitted to the diagnostic system, it is installed as indicated at step 452. Again, the subscription data, both at the diagnostic system and at the service facility, is updated to indicate the current status of the program at step 454 as described above.

What is claimed is:

1. A service platform for a medical diagnostic system, the service platform comprising:
    signal acquisition interface circuitry for accessing image data generated by the medical diagnostic system;
    user interface circuitry coupled to the signal acquisition interface circuitry for formulating service requests for operational servicing of the diagnostic system and viewing service messages in response to such requests; and
    communications circuitry coupled to the user interface circuitry and the signal acquisition interface circuitry for transmitting service requests and image data to a remote service location and receiving service messages from the remote service location.

2. The service platform of claim 1, further comprising a subscription management circuit for storing and accessing data representative of service subscriptions of a diagnostic system.

3. The service platform of claim 1, wherein the user interface circuitry and the communications circuitry are adapted for use with a plurality of diagnostic system modalities.

4. The service platform of claim 1, wherein the signal acquisition interface circuitry is adapted for use with a specific system modality.

5. The service platform of claim 1, wherein the user interface circuitry includes a browser adapted to display a plurality of user viewable pages for formulating the service requests and viewing the service messages.

6. The service platform of claim 5, further comprising a server coupled to the browser for accessing service data and messages in response to user commands received via the browser.

7. The service platform of claim 6, wherein the server is configured to exchange service data between the signal acquisition interface circuitry and the communications circuitry.

8. The service platform of claim 1, wherein the signal acquisition interface circuitry includes translation circuitry for converting scanner data to a desired data format.

9. A service platform for a plurality of medical diagnostic systems, the platform comprising:
    a modality interface module for exchanging operational parameter data with medical diagnostic equipment;
    a server coupled to the modality interface module for coordinating exchange of operational parameter data between the modality interface module and external circuitry;
    a user interface coupled to the server and configured to display a plurality of user interface pages for managing service of the equipment, for formulating service requests for operational servicing of a medical diagnostic system and for viewing service messages in response to such requests; and
    a communications module coupled to the server for transmitting and receiving service data, service requests and service messages between the diagnostic system and a remote location.

10. The service platform of claim 9, modality interface module is adaptable for a plurality of equipment modalities.

11. The service platform of claim 10, wherein the plurality of equipment modalities includes a magnetic resonance modality, a computed tomography modality and an x-ray modality.

12. The service platform of claim 10, wherein the modality interface module includes an adapter module for translating the operational parameter data from a first format to a second format.

13. The service platform of claim 12, wherein the first format includes a DICOM format and the second format includes a format permitting an image to be viewed on a browser.

14. The service platform of claim 9, further comprising a subscription module coupled to the server for storing and accessing service subscription data for the diagnostic system.

15. The service platform of claim 9, further comprising an alternative communications module for exchanging data with external circuitry other than via the communications module.

16. The service platform of claim 9, wherein the communications module includes a modem for exchanging service data over a network.

17. A medical diagnostic service system, the system comprising:

a first station of a first modality;

a second station of a second modality different from the first modality; and a service platform installed on the first and the second stations, the service platform including a modality interface module for exchanging data with the first or the second station, for formulating service requests for operational servicing of the respective first or second station and for viewing service messages in response to such requests, a server coupled to the modality interface module for coordinating exchange of the data, and communications circuitry coupled to the server for exchanging the data, service requests and service messages with external devices via a network.

18. The system of claim 17, wherein the modality interface module of the first station is adapted to the first modality and the modality interface module of the second station is adapted to the second modality.

19. The system of claim 17, further comprising a user interface coupled to the server for displaying and receiving service data for the respective station.

20. The system of claim 19, wherein the user interface includes a browser configured to display a plurality of user viewable service pages.

21. The system of claim 19, wherein the user interface of the first station is adapted to the first modality and the user interface of the second station is adapted to the second modality.

22. The system of claim 17, wherein the first modality is a magnetic resonance imaging modality.

23. The system of claim 17, wherein the first modality is a computed tomography imaging modality.

24. The system of claim 17, wherein the first modality is an x-ray imaging modality.

25. The system of claim 17, wherein the platform further includes a service request module for generating a service request without operator intervention by monitoring operational parameters of a diagnostic station.

26. The system of claim 25, wherein the operational parameters are configurable by modality.

27. A system for providing service to a plurality of medical diagnostic stations, the system comprising:

a first station of a first modality;

a second station of a second modality different from the first modality;

a field service unit; and a uniform service platform installed on the first station, the second station and the field service unit, the uniform service platform being configured to exchange service data between the stations and the field service unit and to permit formulation of service requests for operational servicing of one of the first or the second stations and viewing of service messages at the stations and the field service unit in response to such requests.

28. The system of claim 27, wherein the uniform service platform includes a server, a user interface coupled to the server for displaying service data, and a communications module for exchanging the service data with external circuitry.

29. The system of claim 28, wherein the user interface includes a browser for displaying a plurality of user viewable pages for display and receipt of service data.

30. The system of claim 27, wherein the uniform service platform includes a modality interface module for accessing operational parameter data from the first and second scanners.

31. The system of claim 30, wherein the modality interface module includes an adapter module for converting data from a first format to a second format.

32. The system of claim 27, wherein the first modality is a magnetic resonance imaging modality.

33. The system of claim 27, wherein the first modality is a computed tomography imaging modality.

34. The system of claim 27, wherein the first modality is an x-ray imaging modality.

* * * * *